(12) United States Patent
Watanabe et al.

(10) Patent No.: US 11,690,930 B2
(45) Date of Patent: Jul. 4, 2023

(54) PHOTOCATALYTIC DEVICE

(71) Applicant: APS Japan Co., Ltd., Osaka (JP)

(72) Inventors: Teruo Watanabe, Osaka (JP);
Hidemitsu Watanabe, Osaka (JP);
Hiroyuki Watanabe, Osaka (JP);
Takafumi Watanabe, Osaka (JP)

(73) Assignee: APS JAPAN CO., LTD., Osaka (JP)

( * ) Notice: Subject to any disclaimer, the term of this patent is extended or adjusted under 35 U.S.C. 154(b) by 0 days.

(21) Appl. No.: 16/771,089

(22) PCT Filed: Dec. 10, 2018

(86) PCT No.: PCT/JP2018/045300
§ 371 (c)(1),
(2) Date: Jun. 9, 2020

(87) PCT Pub. No.: WO2019/117081
PCT Pub. Date: Jun. 20, 2019

(65) Prior Publication Data
US 2021/0187152 A1  Jun. 24, 2021

(30) Foreign Application Priority Data
Dec. 11, 2017 (JP) ................................ 2017-236969

(51) Int. Cl.
*A61L 9/20* (2006.01)
*B60H 3/06* (2006.01)

(52) U.S. Cl.
CPC ............. *A61L 9/205* (2013.01); *B60H 3/06* (2013.01); *B60H 2003/0675* (2013.01)

(58) Field of Classification Search
CPC .................. A61L 9/205; B60H 2003/0675
See application file for complete search history.

(56) References Cited

U.S. PATENT DOCUMENTS 8,585,980 B2 * 11/2013 Tupman .................. A61L 9/205
422/122
2002/0081246 A1 6/2002 Tsukada
(Continued)

FOREIGN PATENT DOCUMENTS

JP   H11-183728 A   7/1999
JP   2007-130562 A  5/2007
(Continued)

OTHER PUBLICATIONS

International Search Report for International Application No. PCT/JP2018/045300 dated Feb. 12, 2019 (4 sheets, 2 sheets translation, 6 sheets total).
(Continued)

*Primary Examiner* — Timothy C Cleveland
(74) *Attorney, Agent, or Firm* — Kratz, Quintos & Hanson, LLP

(57) ABSTRACT

In a photocatalytic device, a photocatalytic filter is formed of a corrugated member and a gas is allowed to flow over front and rear surfaces of the filter from one end toward the other end thereof along a direction in which ridges and valleys extend, and a gas inflow part and a gas outflow part are provided at both end positions of a photocatalytic filter instead of providing a gas inlet-side flow channel and a gas output-side flow channel at positions facing filter surfaces. Thus, a contact area between a gas and the filter surfaces can be maintained, and miniaturization of the device such as reduction in the thickness or diameter can be realized without increasing gas circulation resistance. In addition, enhanced light irradiation efficiency, simplified structure, energy saving, and cost reduction can be realized. Moreover, the problem of heat can be solved.

2 Claims, 16 Drawing Sheets

(56) References Cited

U.S. PATENT DOCUMENTS

2006/0124442 A1* 6/2006 Valpey, III ........... B01D 53/007
                                                     204/157.15
2018/0250431 A1* 9/2018 Eide ..................... B01D 53/007
2018/0344890 A1   12/2018 Watanabe

FOREIGN PATENT DOCUMENTS

| JP | 2010-117936 A | 5/2010 |
| JP | 2012-179530 A | 9/2012 |
| JP | 2013-169502 A | 9/2013 |
| JP | 2017-001026 A | 1/2017 |
| JP | 2017-148705 A | 8/2017 |
| WO | 2017/099231 A1 | 6/2017 |

OTHER PUBLICATIONS

Written Opinion of the International Searching Authority for International Application No. PCT/JP2018/045300 dated Feb. 12, 2019 (4 sheets).

* cited by examiner

PHOTOCATALYTIC DEVICE

TECHNICAL FIELD

The present invention relates to a photocatalytic device including: a photocatalytic filter on which a photocatalyst is carried; and a light irradiation unit which irradiates a surface of the photocatalytic filter with ultraviolet light or visible light.

BACKGROUND ART

As for this type of photocatalytic device, Patent Literature 1, for example, has proposed a photocatalytic device including: a housing that allows a gas to circulate therein; a photocatalytic filter disposed in the housing; and a light irradiation unit including first and second irradiation parts that are alternately arranged in parallel, have a plurality of photodiodes mounted on a substrate, and irradiate the surface of the photocatalytic filter with light.

Thus, the conventional photocatalytic device is generally configured to allow a gas to pass through vent holes of a photocatalytic filter while irradiating a filter surface of the photocatalytic filter with light, thereby decomposing and eliminating a harmful substance, an odor, etc., in the gas by the photocatalyst during the circulation of the gas. This configuration of the conventional photocatalytic device requires an inlet-side flow channel and an outlet-side flow channel to be provided for allowing the gas to smoothly pass through the vent holes on both sides of the photocatalytic filter so as to face the entire filter surfaces. Such flow channels result in the increase in device dimensions in the filter thickness direction.

In the inlet-side or outlet-side flow channel, it is also necessary to provide an irradiation unit for irradiating the fitter surface with light. Since this irradiation unit should not prevent smooth circulation of gas, the structure for irradiating the filter surface with light without increasing gas circulation resistance tends to be complicated as in Patent Literature 1, which may cause an increase in cost and impede improvement of light irradiation efficiency, Consequently, power consumption will be increased for ensuring an amount of light irradiation, and heat generation is also increased.

CITATION LIST

Patent Literature

[PTL 1] Japanese Unexamined Patent Application Publication No. 2013-169502

SUMMARY OF THE INVENTION

Problems to be Solved by the Invention

The present invention has been made in view of the above-described circumstances, and an object of the present invention is to provide a photocatalytic device which realizes miniaturization such as reduction in its thickness or diameter without increasing gas circulation resistance, improves light irradiation efficiency, has a simple structure, realizes energy saving and cost reduction, and solves the problem of heat generation.

Solution to the Problems

The inventors of the present invention have conducted thorough research in view of the above circumstances, and found the facts as follows. A photocatalytic filter includes a corrugated member and a gas is allowed to flow over front and rear surfaces of the filter from one end toward the other end along a direction in which ridges and valleys extend, instead of adopting the conventional configuration in which a gas is allowed to pass through a photocatalytic filter from one surface to the other surface through vent holes so as to penetrate a filter surface. According to the configuration of the present invention, a contact area between the gas and the filter surfaces can be maintained. In addition, a gas inflow part and a gas outflow part are provided at both end positions of a photocatalytic filter instead of providing a gas inlet-side flow channel and a gas output-side flow channel at positions facing filter surfaces. Accordingly, it is possible to allow the gas to flow as described above, and device dimensions in the filter thickness direction can be significantly reduced. The inventors have further found that the above configuration increases the degree of freedom in designing a light irradiation unit, realizes a novel light irradiation mode having higher efficiency with a simple structure, and realizes energy saving and cost reduction. Thus, the present invention has been completed.

That is, the present invention includes the following inventions.

(1) A photocatalytic device includes: a photocatalytic filter having a surface on which a photocatalyst is supported, the photocatalytic filter being formed of a corrugated member having a plurality of ridges and a plurality of valleys alternately arranged, the photocatalytic filter having light-passing holes that allow ultraviolet light or visible light to pass therethrough, at top portions of the ridges and bottom portions of the valleys, a light irradiation unit configured to irradiate one of front and rear surfaces of the photocatalytic filter with ultraviolet light or visible light; a reflection wall facing the other one of the front and rear surfaces of the photocatalytic filter, the reflection wall reflecting light that has been emitted from the light irradiation unit and has passed through the light-passing holes of the ridges and the valleys of the photocatalytic filter, toward the other surface; and a gas inflow part and a gas outflow part respectively provided at one end and the other end of the photocatalytic filter, the gas inflow part and the gas outflow part allowing a gas to flow in a space between the light irradiation unit and the photocatalytic filter and a space between the reflection wall and the photocatalytic filter, over the front and rear surfaces of the photocatalytic filter from the one end toward the other end along a direction in which the ridges and the valleys extend.

(2) The photocatalytic device according to above (1) further includes a metallic support member configured to support the photocatalytic filter at the one end or the other end, wherein the support member supports the light irradiation unit.

(3) In the photocatalytic device according to above (1) or (2), the light irradiation unit includes: a light source disposed at a position corresponding to the one end or the other end of the photocatalytic filter; and a light guide member having a light emitting surface facing the one of the surfaces of the photocatalytic filter, the light guide member taking light emitted from the light source therein, and applying the light to the one of the surfaces of the photocatalytic filter through the light emitting surface.

(4) In the photocatalytic device according to any one of above (1) to (3), the light-passing holes of the photocatalytic filter are through-grooves elongated in the direction in which the ridges and the valleys extend, and upright pieces are formed at paired opening edges which extend along a longitudinal direction of each through-groove and are opposed each other, the upright pieces being cut and raised for forming the through-groove and being erected at a projecting surface of the ridge or the valley.

Advantageous Effects of the Invention

The photocatalytic device according to the present invention configured as described above allows a gas to flow in the direction in which the ridges and the valleys extend, along the filter surfaces on both sides of the photocatalytic filter that is corrugated and therefore has a sufficient surface area, while irradiating the filter surfaces with light. Thus, a harmful substance, an odor, etc., in the gas can be efficiently decomposed and/or eliminated by the photocatalyst.

Furthermore, the gas inlet-side flow channel and outlet-side flow channel which have conventionally been required at the positions facing the filter surfaces are omitted, and the gas-inflow part and the gas outflow part are provided instead of the flow channels, at the both ends of the filter, to circulate the gas as described above. Thus, the device dimensions in the filter thickness direction are significantly reduced, and the degree of freedom in designing the light irradiation unit is increased.

Furthermore, the light-passing holes that allow ultraviolet light or visible light to pass therethrough are formed at the top portions of the ridges and the bottom portions of the valleys, and the photocatalytic device is provided with: the light irradiation unit that irradiates one of the front and rear surfaces of the photocatalytic filter with ultraviolet light or visible light; and the reflection wall that is provided on a side facing the other one of the front and rear surfaces of the photocatalytic filter, and reflects light, which has been emitted from the light irradiation unit and has passed through the light-passing holes, toward the other surface. Therefore, the both filter surfaces can be efficiently irradiated with light, and a light irradiation configuration having high light irradiation efficiency can be realized with the simple structure. Moreover, energy saving and cost reduction can be realized, and heat generation can be reduced. The light-passing holes also allow air to pass therethrough. However, the light-passing holes are not provided as flow channels mainly for gas as in the conventional devices but are provided as holes mainly for light to pass therethrough.

The highly efficient light irradiation configuration realized by the light irradiation unit and the reflection wall is realized by omitting the gas inlet-side flow channel and outlet-side flow channel having been required at the positions facing the filter surfaces as described above, Since the gas flows along the direction in which the ridges and the valleys of the corrugated filter extend, the light irradiation unit and the reflection wall do not impede the gas flow. Therefore, the device dimensions in the filter thickness direction can be reduced by bringing the light irradiation unit and/or the reflection wall close to the filter surface. Therefore, the photocatalytic device can be configured to be suitable for: deodorizing a refrigerating compartment or decomposing VOC in a vegetable compartment in a refrigerator; deodorizing/sterilizing the interior of a vehicle by being fitted in a beverage holder; or deodorizing/sterilizing a small space by being placed at a bedside, in a shoe cabinet, in a closet, on a desk, etc., in a house.

The photocatalytic device is provided with the metallic support member that supports the photocatalytic filter at the one end or the other end, and the support member supports the light irradiation unit. In this configuration, heat generated by the light irradiation unit can be transferred to the metallic photocatalytic filter through the support member, and efficiently dissipated by the gas flowing at the surface of the photocatalytic filter that serves as a heatsink.

Meanwhile, the light irradiation unit includes: the light source disposed at a position corresponding to the one end or the other end of the photocatalytic filter; and the light guide member that has the light emitting surface facing the one of the surfaces of the photocatalytic filter, and that takes light emitted from the light source therein and applies the light to the one of the surfaces of the photocatalytic filter through the light emitting surface. In this configuration, reduction in the thickness of the light irradiation unit can be achieved, whereby the device dimensions in the filter thickness direction can be further reduced. This light guide member can be efficiently used when the gas inlet-side flow channel and outlet-side flow channel having been required at the positions facing the filter surfaces as described above are omitted.

Meanwhile, the light-passing holes of the photocatalytic filter are through-grooves elongated in the direction in which the ridges and the valleys extend, and the upright pieces are formed at the paired opening edges which extend along the longitudinal direction of each through-groove and are opposed each other. The upright pieces are cut and raised for forming the through-groove and are erected at a projecting surface of the ridge or the valley. In this configuration, the photocatalytic filter has a large surface area due to the corrugated surfaces having the ridges and the valleys, and the surface area is further increased by the upright pieces at the opening edges of the through-grooves formed at the ridges or the valleys. Thus, a sufficient content area between the gas and the photocatalytic filter surface can be ensured, whereby a catalytic reaction is performed more efficiently, and more photocatalyst layers can be provided, thereby realizing an excellent purification effect.

Furthermore, since the photocatalytic filter having the through-grooves and the upright pieces formed in the corrugated member can be manufactured through machine work such as pressing, the manufacturing cost can be reduced as compared with a conventional ceramic filter and a filter that requires etching treatment. In addition, since the through-grooves are formed at the top portions of the ridges and the bottom portions of the valleys, the photocatalytic filter is easily deformable, thereby increasing the degree of freedom in shape. Furthermore, since the upright pieces are cut and raised pieces, the maximum contact area can be maintained without wasting the base material. Moreover, the upright pieces can be efficiently and inexpensively formed through machine work.

DESCRIPTION OF EMBODIMENTS

Figure 1:
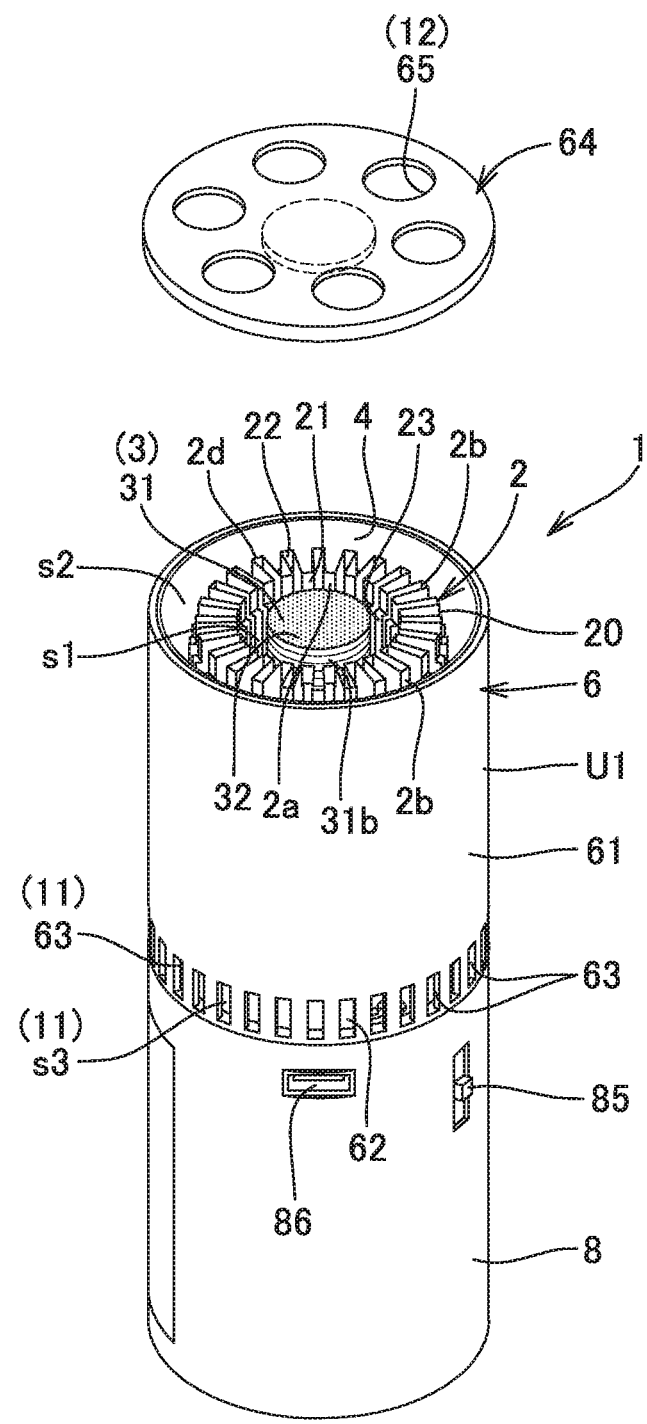
FIG. 1 is a perspective view showing a photocatalytic device with a lid member being separated, according to the first embodiment of the present invention.

Next, embodiments of the present invention will be described in detail with reference to the accompanying drawings. First, the first embodiment will be described with reference to FIGS. 1 to 10.

As shown in FIGS. 1 to 4, a photocatalytic device 1 of the present invention includes a photocatalytic filter 2, a light irradiation unit 3, a reflection wall 4, a gas inflow part 11, and a gas outflow part 12. The photocatalytic filter 2 is formed of a corrugated member 20 having a plurality of ridges 21 and a plurality of valleys 22 alternately arranged. Light-passing holes 23, through which ultraviolet light or visible light passes, are provided at top portions of the ridges 21 and the bottom portions of the valleys 22. A photocatalyst is carried on the surface of the photocatalytic filter 2. The light irradiation unit 3 irradiates one surface 2a of front and rear surfaces of the photocatalytic filter 2 with ultraviolet light or visible light. The reflection wall 4 is provided on a side facing the other surface 2b of the photocatalytic filter 2. The reflection wall 4 reflects the light, which has been emitted from the light irradiation unit 3 and has passed through the light-passing holes 23 of the photocatalytic filter 2, toward the other surface 2b. The gas inflow part 11 and the gas outflow part 12 are respectively provided at one end 2c side and the other end 2d side with respect to the photocatalytic filter 2. These parts 11 and 12 allow a gas to flow through a space s1 between the light irradiation unit 3 and the photocatalytic filter 2 and a space s2 between the photocatalytic filter 2 and the reflection wall 4, over the front and rear surfaces of the photocatalytic filter 2 from the one end toward the other end along the direction in which the ridges and the valleys extend.

Figure 5:
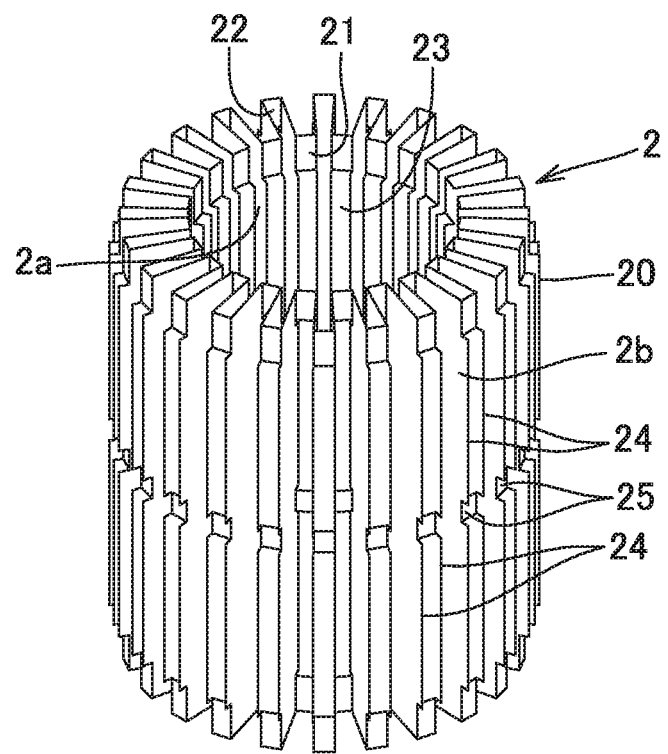
FIG. 5 is a perspective view showing a photocatalytic filter provided in the unit.
Figure 6A:
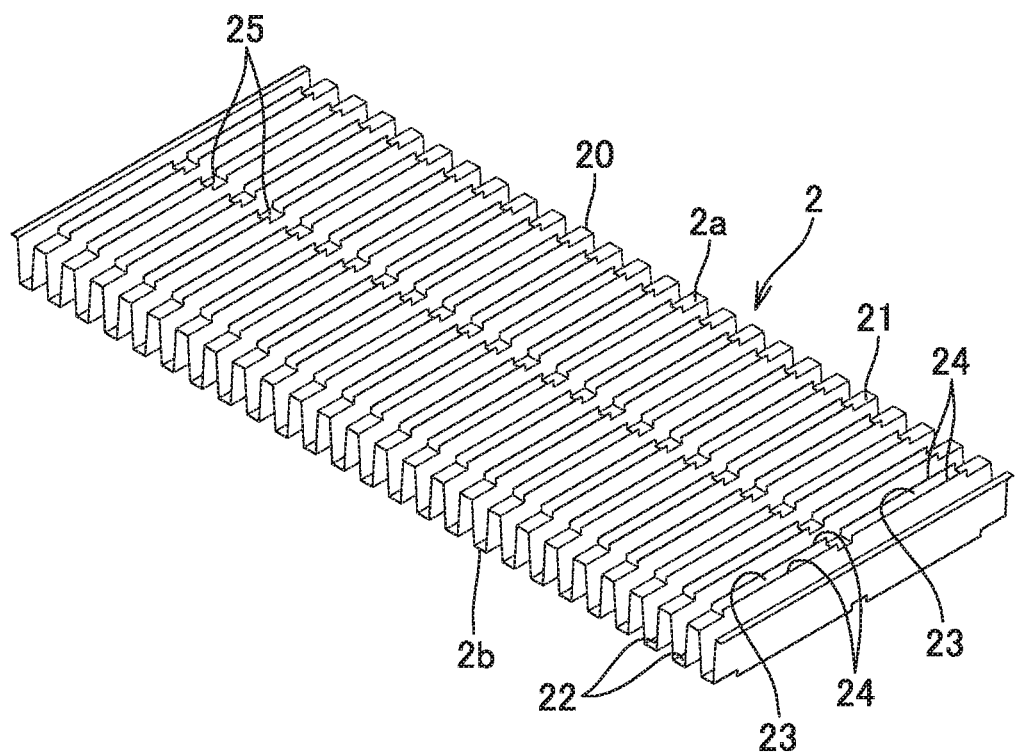
FIG. 6A is a perspective view showing the photocatalytic filter in its flat state before being formed in a cylindrical shape.
Figure 6B:
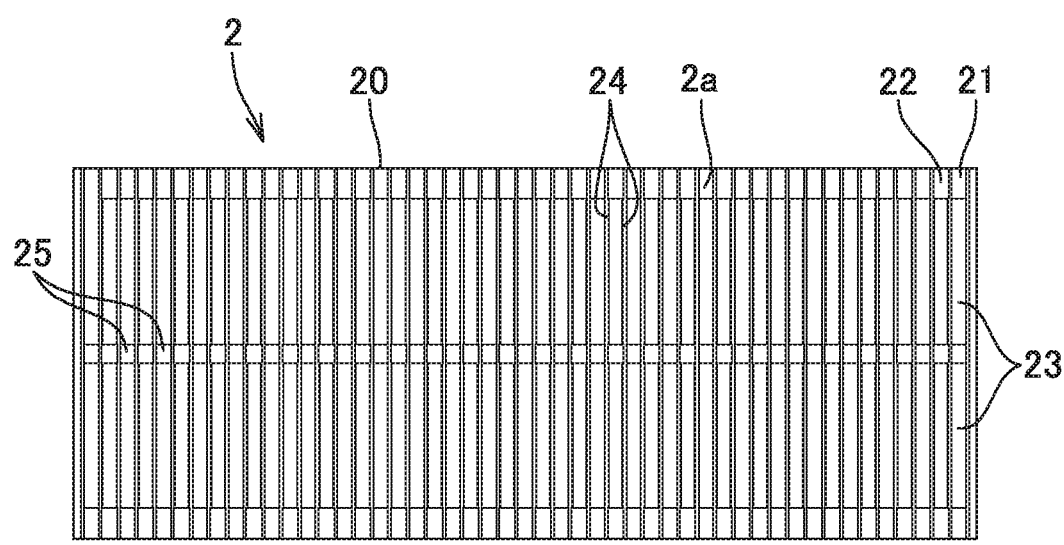
FIG. 6B is a planar view thereof.
Figure 7:
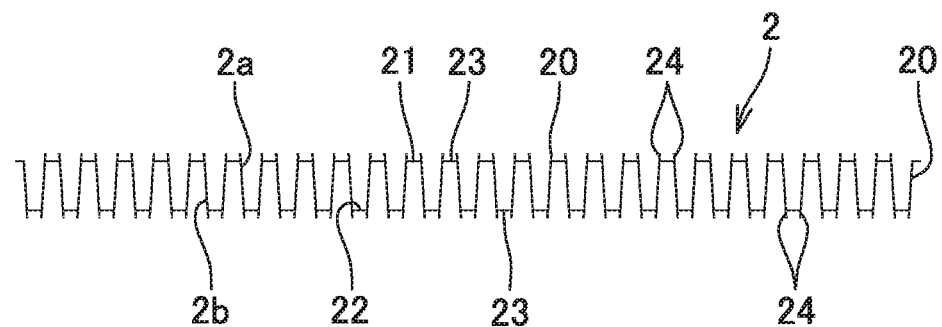
FIG. 7 is a side view of the photocatalytic filter.
Figure 8:
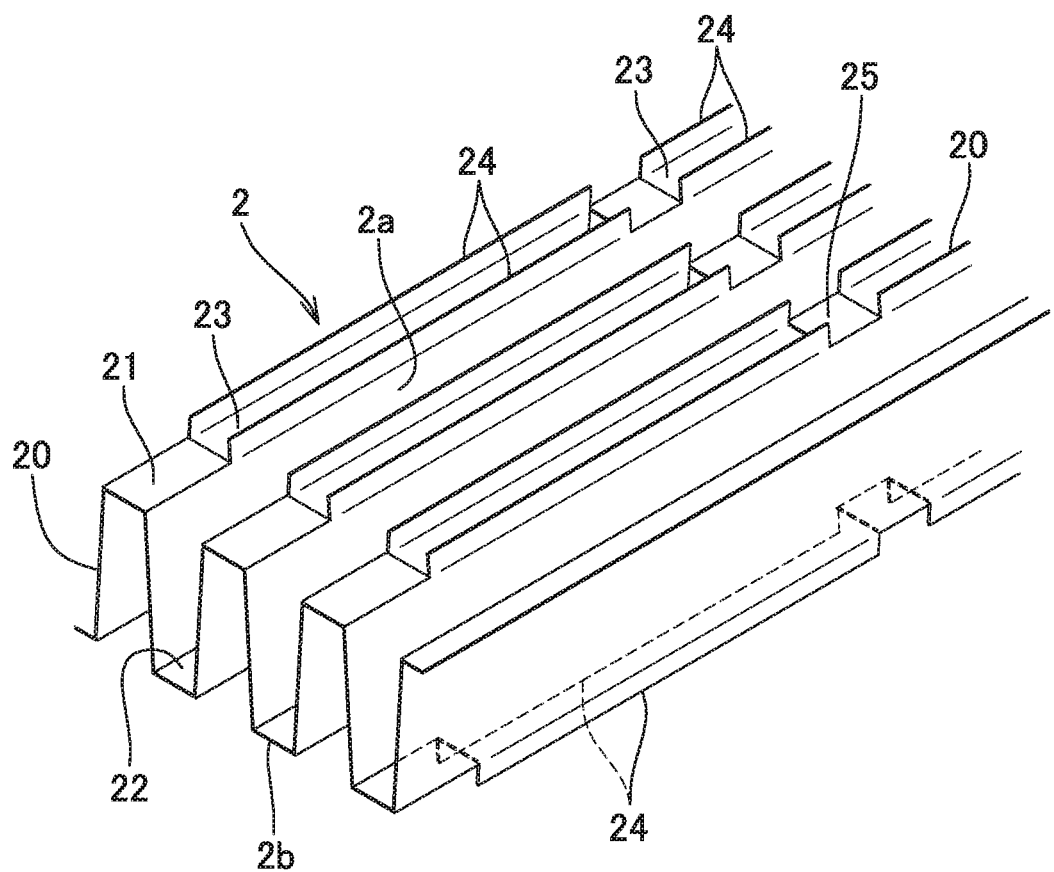
FIG. 8 is a perspective view of a major part of the photocatalytic filter.

With reference to FIGS. 6 to 8, the photocatalytic filter 2 is manufactured as follows. Through a press work, the member 20 is formed into a flat corrugated shape in which all the top portions of the plurality of ridges 21 are positioned on the same plane and all the bottom portions of the plurality of valleys 22 are positioned on the same plane. After being coated with a photocatalyst layer over the entire surface, the corrugated member 20 is rounded in a cylindrical shape around an axis parallel to the direction in which the ridges 21 and the valleys 22 extend, with the one surface 2a, of the front and rear surfaces, facing inward. Then, the ridges 21 or the valleys 22 at the opposed ends are overlapped and connected to each other. Thus, the cylindrical photocatalytic filter 2 shown in FIG. 5 is obtained. This cylindrical photocatalytic filter 2 is housed in a housing 6 having a cylindrical peripheral wall 61, in a manner of being coaxial with the housing 6.

In the present embodiment, the ridges 21 and the valleys 22 each have an angular shape, so that the photocatalytic filter 2 has an angular corrugated shape as a whole. However, the photocatalytic filter 2 may have a non-angular corrugated shape in which ridges and valleys are smoothly continued. As for "ridges" and "valleys", when one of the both surfaces of the corrugated member is an upper surface while the other surface is a lower surface, portions projecting at the upper surface are regarded as "ridges" while portions projecting at the lower surface are regarded as "valleys". Examples of the material of the member may include, but are not limited to, various metal materials such as aluminum and stainless steel.

Not all the ridges 21 and the valleys 22 need to have the light-passing holes 23. For example, the light-passing holes 23 may be provided while skipping every other or every two or more ridges 21 or valleys 22. The dimensions, number, layout, etc., of the light-passing holes 23 can be appropriately determined to attain shape retainability according to the intended use, size, etc., of the device. In this embodiment, for each ridge 21 or valley 22, two light-passing holes 23, being through-grooves elongated in the extending direction of the ridge 21 or valley 22, are continuously formed at an interval, and shape retainability as a whole is maintained by a bridge portion 25 (remaining portion of the ridge 21 or valley 22 between the light-passing holes 23). However, the length, interval, etc., of the light-passing holes 23 can be appropriately determined according to the plate thickness, other dimensions, and the degree of desired shape retainability. For example, three or more light-passing holes 23 may be continuously formed in the column direction, or only one light-passing hole 23 may be formed.

At paired and opposing opening edges extending along the longitudinal direction of each light-passing hole 23, upright pieces 24 are provided so as to erect from the projecting surface of the ridge 21 or the valley 22. The upright pieces 24 are cut and raised for forming the light-passing holes 23. The photocatalytic filter 2 having the upright pieces 24 thus formed has a large surface area contacting the gas due to the surfaces of the corrugated member having the ridges 21 and the valleys 22, and simultaneously, the contact area with the gas and light is increased by the inner surfaces of the light-passing holes 23 formed in the ridges 21 or the valleys 22, and the upright pieces 24 at the opening edges. This allows catalytic reaction to be efficiently performed. As mentioned above, the upright pieces 24 are erected from the projecting surface of the ridge 21 or the valley 22, whereby the upright pieces 24 do not impede incoming light. Accordingly, the catalyst layer formed on the corrugated surfaces, the inner surfaces of the through-grooves, and the surfaces of the upright pieces 24 are efficiently irradiated with the light.

The upright pieces 24 can be efficiently formed through cutting and raising work using punching, simultaneously with or immediately after the press work to form the corrugated shape. Although the upright pieces 24 formed at the opposing opening edges are long pieces extending over almost the entire lengths of the respective opening edges, a plurality of upright pieces 24 may be provided at intervals. In this case, upright pieces 24 having a long projection length may be formed alternately (zigzag) at the opposing opening edges through cutting and raising work. The cut pieces are raised toward the both sides from the center, so that the upright pieces 24 provided at the opposing opening edges have the same height, specifically, about half the dimension of the through-groove in the width direction orthogonal to the column direction thereof. The cutting and raising work is adopted, whereby the upright pieces 24 can be formed without wasting the base material, and the contact area can be increased to the maximum.

The photocatalyst layer is obtained by carrying photocatalyst particles, such as particles of an ultraviolet-excitation type photocatalyst such as titanium oxide or particles of a visible-light-excitation type photocatalyst mainly composed of tungsten trioxide, on the surface of the member. The base member into the corrugated shape having the ridges 21 and the valleys 22 may be formed through press work. In such a case, if the photocatalyst layer has been formed on the surface of the member in advance, the photocatalyst layer may be peeled off or may cause degradation of shape accuracy. In order to avoid this, the photocatalyst layer should be formed after the press work to form the corrugated shape. The method for carrying the photocatalyst particles (photocatalyst layer formation method) is not particularly limited. Preferably, a slurry dipping method, which is relatively low in cost, is adopted. Other dipping methods, vacuum impregnation, a sol-gel method, etc., may also be adopted.

Figure 3:
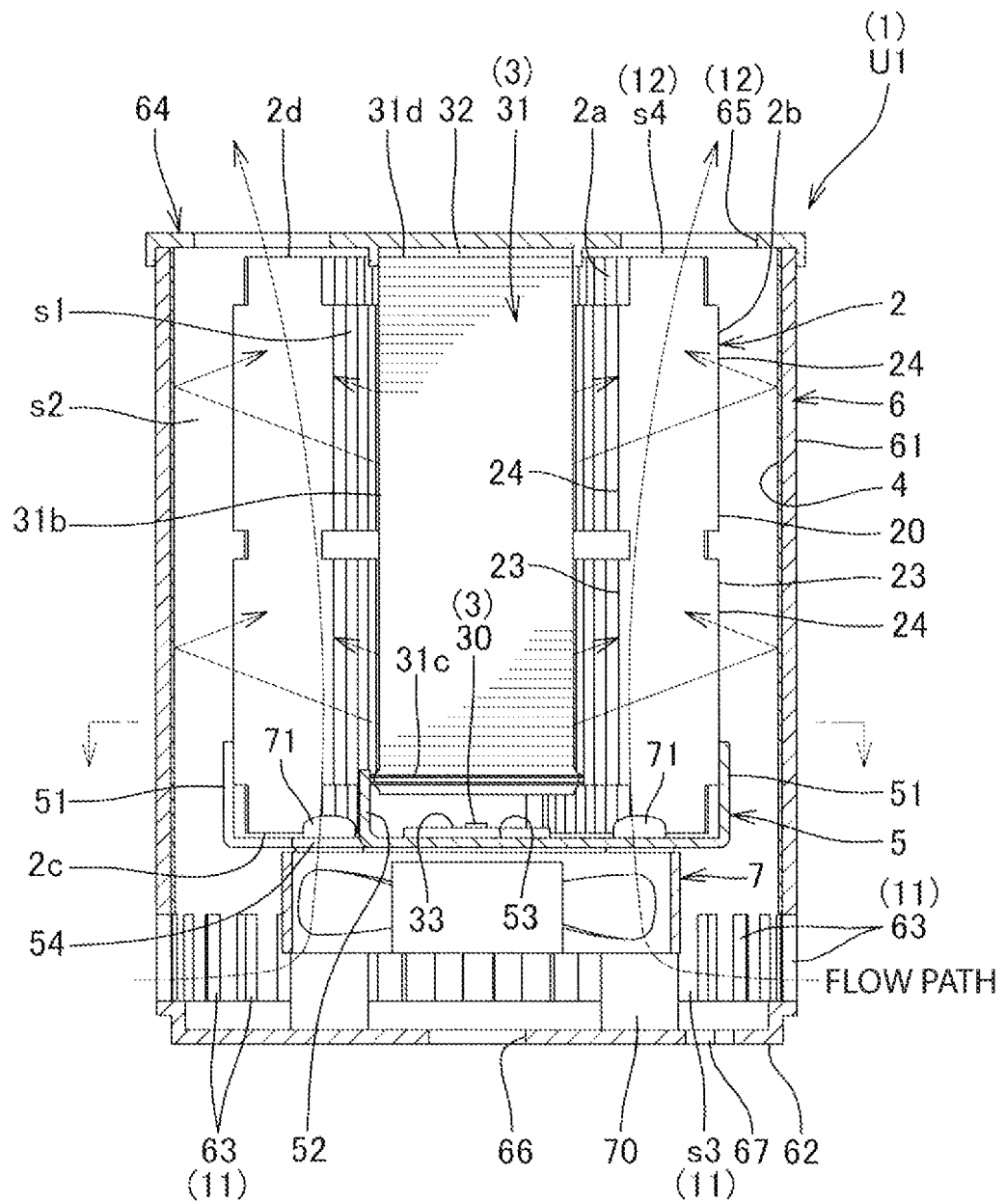
FIG. 3 is a vertical cross-sectional view of a photocatalytic device unit constituting the photocatalytic device.
Figure 4:
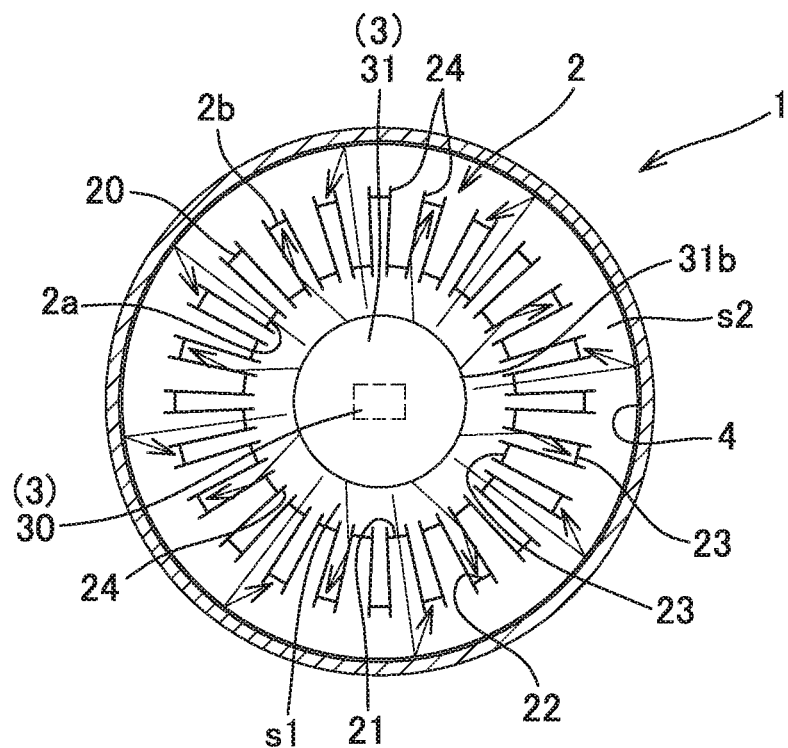
FIG. 4 is a horizontal cross-sectional view of the unit.

As shown in FIG. 3 and FIG. 4, the light irradiation unit 3 is disposed at the center position in the housing C. The light irradiation unit 3 emits light outward to irradiate, with the light, the one surface 2a, facing inward, of the cylindrical photocatalytic filter 2 facing the light irradiation unit 3. The light irradiation unit 3 is provided over an area of almost the same length as the photocatalytic filter 2 in the axial direction so as to irradiate the entire surface 2a of the photocatalytic filter 2 almost uniformly with the light. In this embodiment, the light irradiation unit 3 includes a columnar light guide member 31 that has the aforementioned length and has a light emitting surface at an outer peripheral surface 31h facing the filter surface 2a. The light irradiation unit 3 further includes a light source 30 disposed at one end 31c side of the light guide member 31. Thus, light emitted from the light source 30 is taken into the light guide member 31, and the light is applied to the filter surface 2a through the light emitting surface (outer peripheral surface 31b).

Instead of using the light guide member 31, a plurality of LED substrates, each having the aforementioned length and including LED elements as light sources disposed at predetermined intervals along the axial direction, may preferably be arranged in different directions so as to irradiate the entire surface of the surrounding filter surface 2a with light. However, the light emission unit having the light guide member and the light source disposed at one end side of the light guide member as in the present embodiment can emit light more uniformly to the surroundings and allow the light source that generates heat to be locally disposed. Moreover, generated heat can be efficiently dissipated through a support member 5 and the like described later. Therefore, the configuration according to the present embodiment is more preferable.

The light guide member 31 has a cylindrical shape, and includes a light shielding layer 32 whose inner surface serves as a reflection surface, at the other end 31d opposite to the one end that faces the light source 30. As for the light source 30, an LED element that emits ultraviolet light or visible light having a wavelength suitable for the photocatalyst of the photocatalytic filter 2 is adopted, and an LED substrate 33 having the LED element is disposed facing the one end of the light guide member 31.

Figure 2:
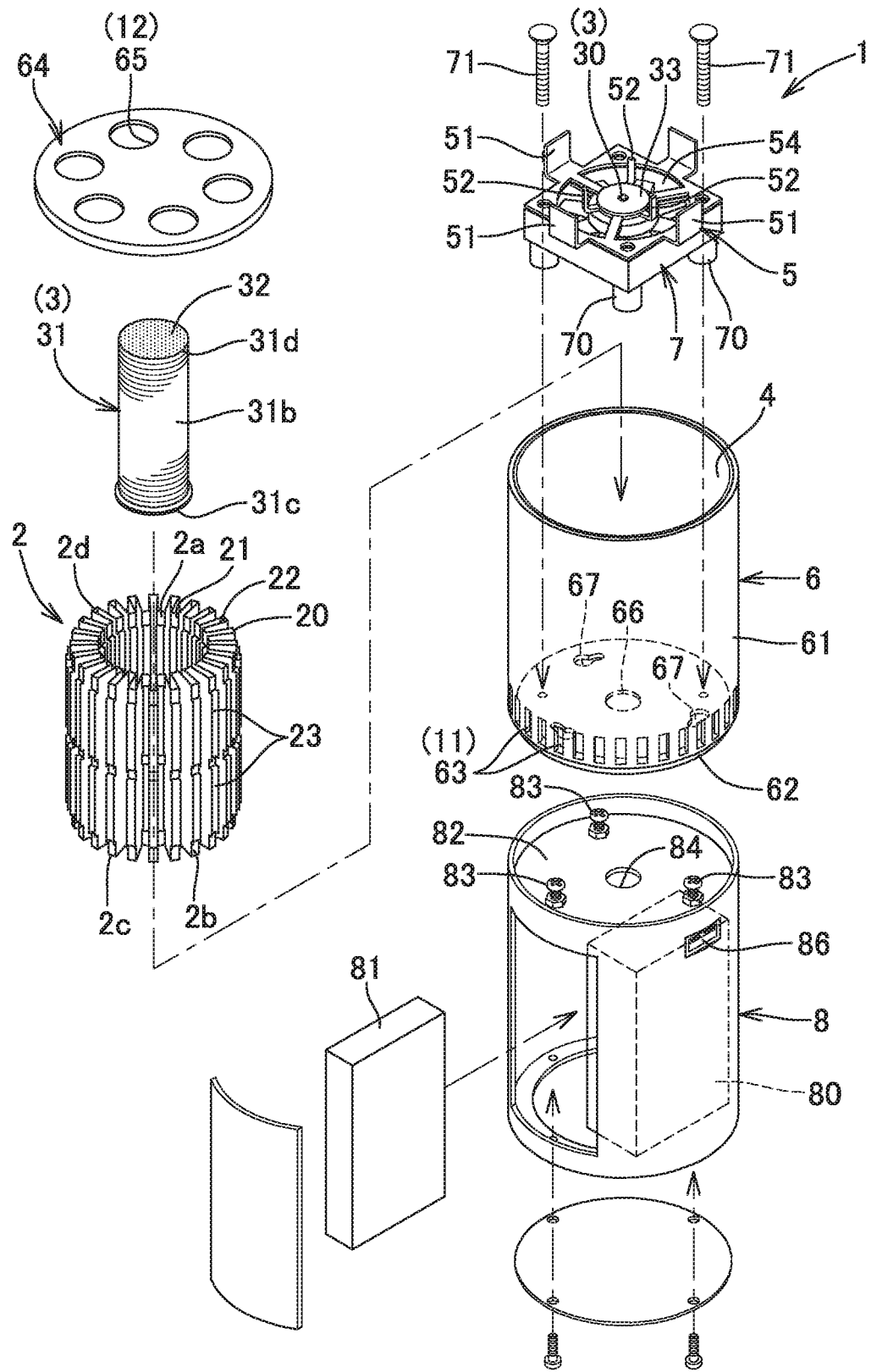
FIG. 2 is an exploded perspective view of the photocatalytic device.

As shown in FIG. 2 and FIG. 3, the photocatalytic filter 2 and the light irradiation unit 3 are coaxially supported by a common support member 5 made of metal. Specifically, the support member 5 has: first holding pieces 51 provided at an outer position and projecting so as to hold the outer peripheral surface of a portion at the one end 2c (lower end in the drawings) of the photocatalytic filter 2; and second holding pieces 52 provided at an inner position and projecting so as to hold the outer peripheral surface of a portion at the one end 31c (lower end in the drawings) of the light guide member 31 of the light irradiation unit 3. In a center area surrounded by the second holding pieces 52, a mounting surface 53 on which the LED substrate 33 is mounted is provided.

The light emitted from the light emitting surface (outer peripheral surface 31b) of the light guide member 31 and applied to the filter surface 2a activates the photocatalyst on the fitter surface 2a, passes through the light-passing holes 23 of the filter 2 to reach the other surface 2b, is reflected by the reflection wall 4 that is the inner peripheral surface of the peripheral wall 61 of the housing, is applied to the entirety of the other surface 2b of the photocatalytic filter 2, and activates the photocatalyst on the surface 2b. As for the reflection wall 4; the surface of the metal material of the housing may be used as it is or after being subjected to mirror finishing, or a mirror sheet may be adhered to the inner surface of the peripheral wall 61.

Since the photocatalytic filter 2 and the light irradiation unit 3 are supported by the metallic support member 5, heat generated in the light irradiation unit 3 is transferred to the metallic photocatalytic filter 2 through the support member 5, and is efficiently discharged from the surface of the photocatalytic filter 2 into the gas. That is, according to the present embodiment, the support member 5 and the photocatalytic filter 2 can efficiently function as heatsinks. In particular, in this embodiment, since the heat of the light irradiation unit 3 is generated from the LED substrate 33, the heat is efficiently transferred to the support member 5 to which the LED substrate 33 is directly mounted.

A vent hole 54 is provided in an area between the outer position where the first holding pieces 51 of the support member 5 are provided and the inner position where the second holding pieces 52 of the support member 5 are provided. The vent hole 54 allows the gas to flow into a space s1 between the inner surface 2a of the supported photocatalytic filter 2 and the outer peripheral surface 31b of the light guide member 31. In this embodiment, the support member 5 is mounted on a bottom plate 62 of the housing 6 via a fan 7 that forcibly feeds the gas into the vent hole 54.

The fan 7 is provided with a plurality of cylindrical leg members 70 disposed spaced apart from each other. The fan 7 and the support member 5 disposed above the fan 7 are screwed onto the housing bottom plate 62 by means of mounting screws 71 via the leg members 70. In an end portion of the peripheral wall 61 of the housing connected to the bottom plate 62, a plurality of ventilation windows 63 penetrating through the housing 6 are formed at intervals in the housing circumferential direction, whereby the gas can be taken into a housing bottom space from the outside of the housing. The fan 7 draws the external gas into the housing 6 through the ventilation windows 63, and further takes the gas through the space between the leg members 70 to feed the gas into the space s1. A space s2 is provided between the outer surface 2b of the photocatalytic filter 2 supported by the support member 5 and the inner surface of the peripheral wall 61 of the housing, and part of the external gas taken through the ventilation windows 63 flows into the space s2.

A lid member 64 is mounted to an end portion of the peripheral wall 61 of the housing opposite to the bottom plate 62 (upper side in the drawings). The lid member 64 has penetrating ventilation windows 65 that allow the spaces s1, s2 to communicate with the outside of the housing. Thus, the gas, which has entered the housing through the ventilation windows 63 and has flowed into the spaces s1, s2 from the housing bottom side, i.e., the one end 2c side of the photocatalytic filter 2, flows in the spaces s1, s2 toward the other end 2d along the direction in which the ridges 21 and the valleys 22 of the photocatalytic filter 2 extend, and thereafter, the gas is discharged to the outside of the housing through the ventilation windows 65.

While flowing in the spaces s1, s2, the gas efficiently contacts the corrugated front and rear surfaces 2a, 2b of the photocatalytic filter 2, and is efficiently purified by the photocatalyst on the front and rear surfaces 2a, 2b which is activated while being irradiated with light. The ventilation windows 63 that allow the gas to flow into the housing, and a space s3 between the ventilation windows 63 and the one end 2c of the photocatalytic filter function as gas inflow parts 11, while a space s4 between the other end 2d of the photocatalytic filter and the lid member 64, the ventilation windows 65 of the lid member, and the like function as gas outflow parts 12.

Thus, in the housing 6, light is radially applied to the photocatalytic filter 2 that is rounded in a cylindrical shape and disposed coaxially with the housing 6, from the inner side toward the outer side, and the inner and outer surfaces of the photocatalytic filter 2 are irradiated with the light through the light-passing holes 23. Meanwhile, the gas flows through the spaces s1, s2 serving as flow channels at both the front and rear surfaces along the axial direction (direction in which the ridges 21 and the valleys 22 extend) intersecting the radial direction, and the gas is efficiently purified by the activated photocatalyst while the gas flows. In the present invention, this intersecting configuration allows the spaces s1, s2 to be set small, whereby the whole device can be miniaturized.

The light-passing holes 23 are through-holes, and not only the light but also the gas is allowed to come and go between the space s1 and the space s2 through the holes. A transparent film may be adhered to the holes to allow only the light to pass therethrough while preventing the gas from passing therethrough. The ventilation windows 63, 65 are preferably provided with dust collecting filters having light shielding property to prevent ultraviolet light or the like from leaking outside, and the dust collecting filters preferably support the photocatalyst.

The fan 7 is a means for forcing the gas to flow into the flow channels formed by the spaces s1, s2 in the housing 6. The fan 7 may be omitted, or placed at the other end side in the housing 6 or outside the housing 6. A through-hole 66 at the center of the bottom plate 62 is a hole through which wires for supplying power to the LED substrate 33 of the light irradiation unit 3 and the fan 7 pass.

In the present embodiment, the housing 6 having the photocatalytic filter 2 and the light irradiation unit 3 disposed therein constitutes a single photocatalytic device unit U1 that functions as a photocatalytic device when externally supplied with power.

Reference numeral 8 denotes a power supply case in which a control board 80, a battery 81, etc., are provided. The power supply case 8 is coaxially and detachably connected to the bottom plate 62 of the photocatalytic device unit U1 constituted by the aforementioned housing 6. A power supply switch 85 and a USB connector 86 are exposed at the outer peripheral surface of the power supply case 8, so that the battery 81 being housed in the case 8 can be charged through a USB cable. Preferably, the power supply case 8 is further provided with an odor sensor, and on-off control may be performed based on an output from the sensor to save power. Thus, the unit U1 and the power supply case 8 configured to be detachable from each other enables a user to replace the power supply case 8 with an auxiliary one and continue to use the unit U1 when the battery power has been consumed. Thus, convenience is improved.

As shown in FIG. 2, on a connection-side upper plate 82 of the power supply case 8, engagement projections 83, which are heads of connection bolts, are provided so as to be detachably engaged with hook slots 67 formed at corresponding positions on the unit U1 side bottom plate 62. Thus, the unit U1 and the power supply case 8 are rotated and connected to each other. Likewise, a through-hole 84 is formed in the upper plate 82 at a position corresponding to the through-hole 66 of the bottom plate 62. Through the through-hole 84, wires (not shown) of the light source 30 and the fan 7 on the unit U1 side can be drawn into the power supply case 8 and detachably connected to the corresponding wires (not shown) with connectors or the like.

Figure 9:
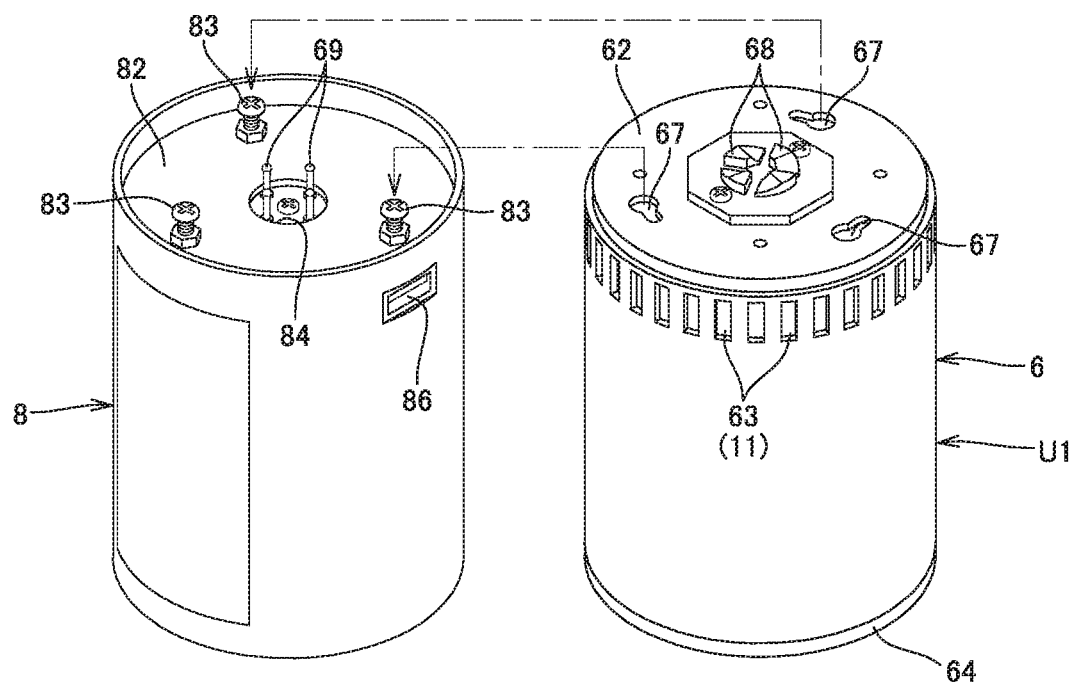
FIG. 9 is a perspective view showing a state where the unit constituting the photocatalytic device is separated from a power supply case.

Electrical connection of the light source 30 and the fan 7 on the unit U1 side with the power supply case 8 side is not limited to the connection through the wires as described above. For example, as shown in FIG. 9, connection terminals 68, 69 are preferably provided on the lower surface of the bottom plate 62 and the upper surface of the upper plate 82, which face each other, so that the corresponding terminals are electrically connected to each other when the unit U1 and the power supply case 8 are rotated and connected as described above. Thus, the work of connecting wires with connectors becomes unnecessary, and mounting/dismounting of the unit U1 on/from the power supply case 8 is facilitated. In this embodiment, one of the two types of connection terminals (connection terminal 69 on the upper plate 82) is a spring pin type connector while the other connection terminal (connection terminal 68 on the bottom plate 62) is a terminal plate having a slope on which the spring pin type connector climbs and presses the terminal plate due to the rotation/connection described above. However, the present invention is not particularly limited to this combination.

When the connection terminals 68, 69 are electrically connected to each other as shown in FIG. 9, positive/negative terminals for the light source 30 and positive/negative terminals for the fan 7 need to be matched in a one-to-one correspondence. Therefore, combinations of the hook slots 67 with the corresponding engagement projections 83 need to be fixed. For this purpose, preferably, the hook slots 67 and the engagement projections 83 are not disposed at equal intervals but are disposed at positions shifted in the circumferential direction or the radial direction. Thus, combinations of the hook slots 67 with the corresponding engagement projections 83 can be fixed while using the hook slots 67 having the same shape and structure and the engagement projections 83 having the same shape and structure.

Figure 10:
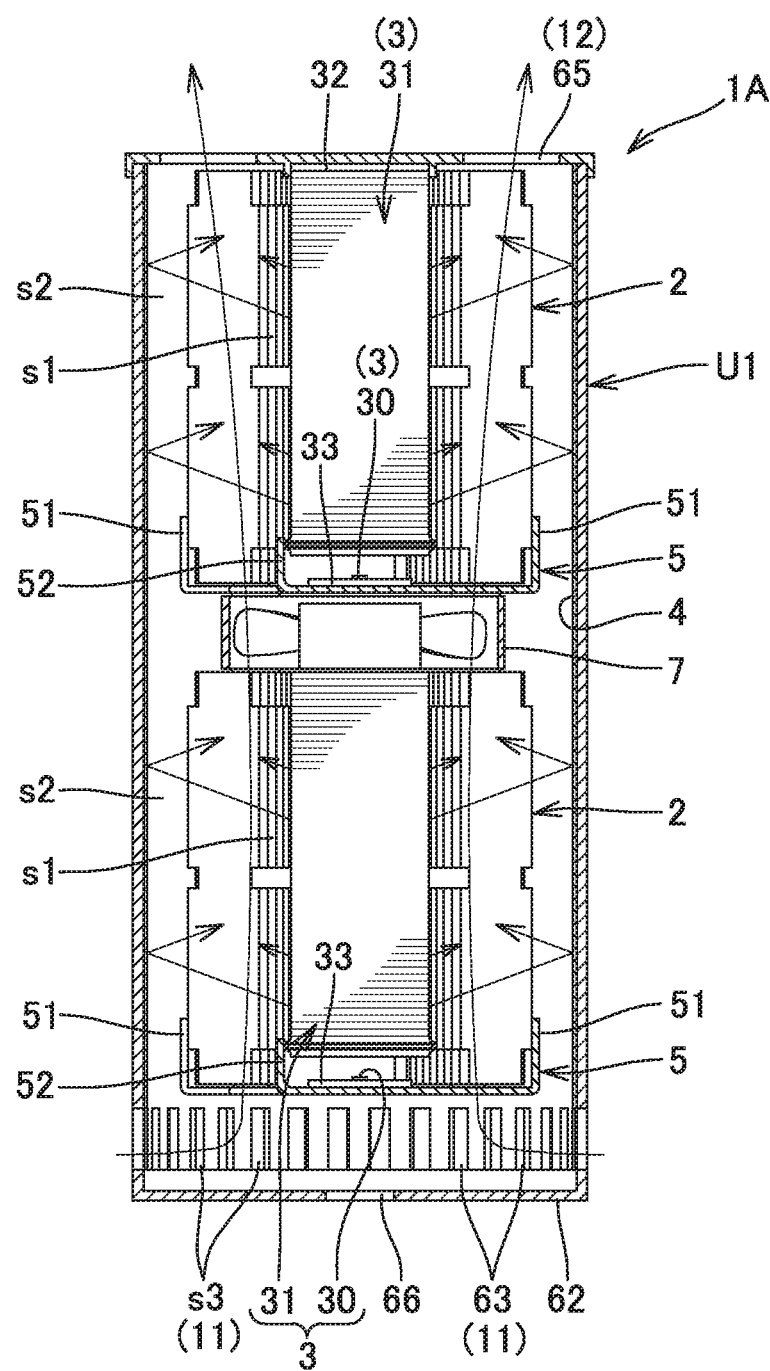
FIG. 10 shows a unit including two photocatalytic filters, as a modification of the above unit.
Figure 11:
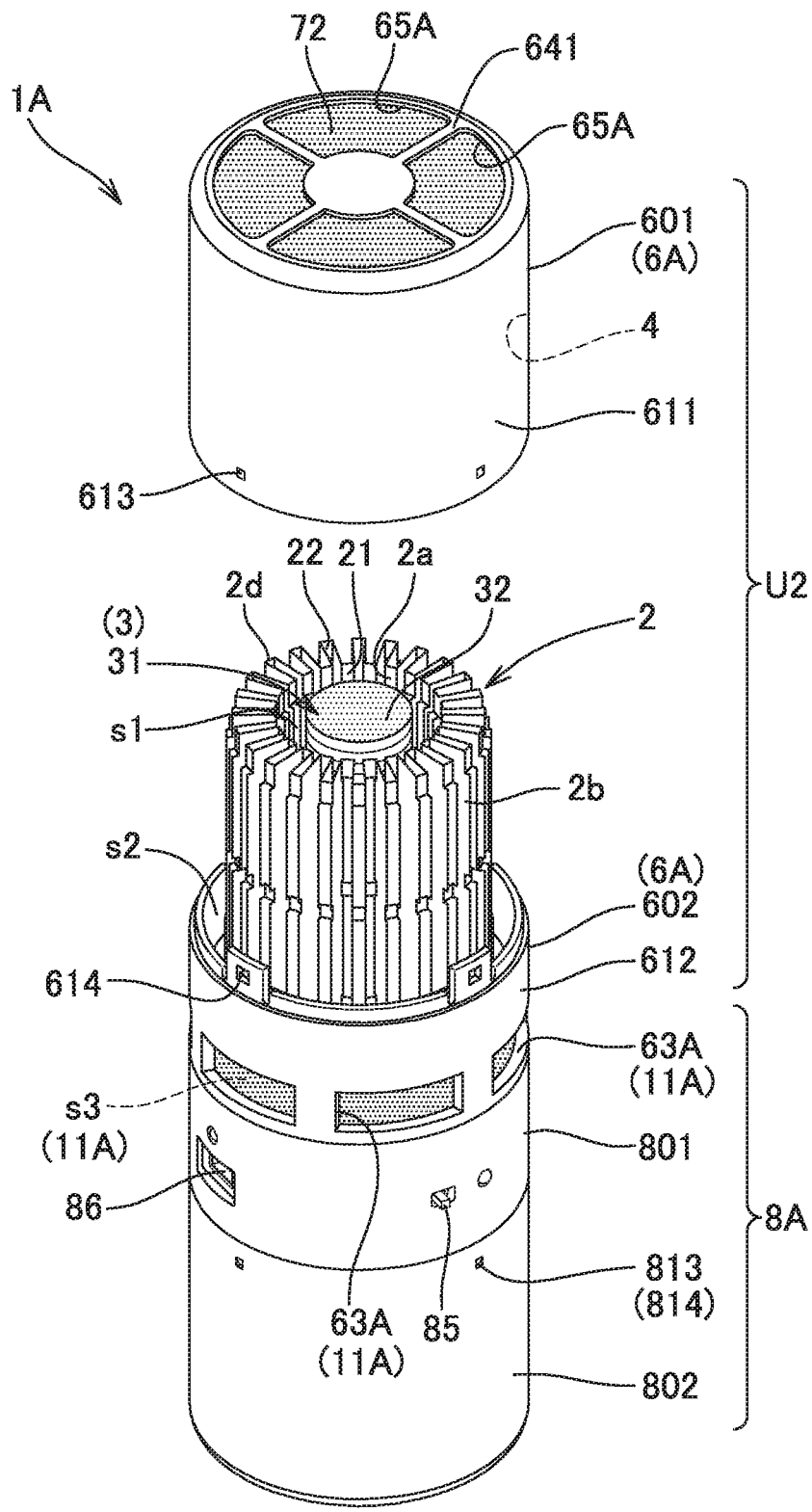
FIG. 11 is a perspective view showing a photocatalytic device with an upper housing being separated, according to the second embodiment of the present invention.
Figure 12:
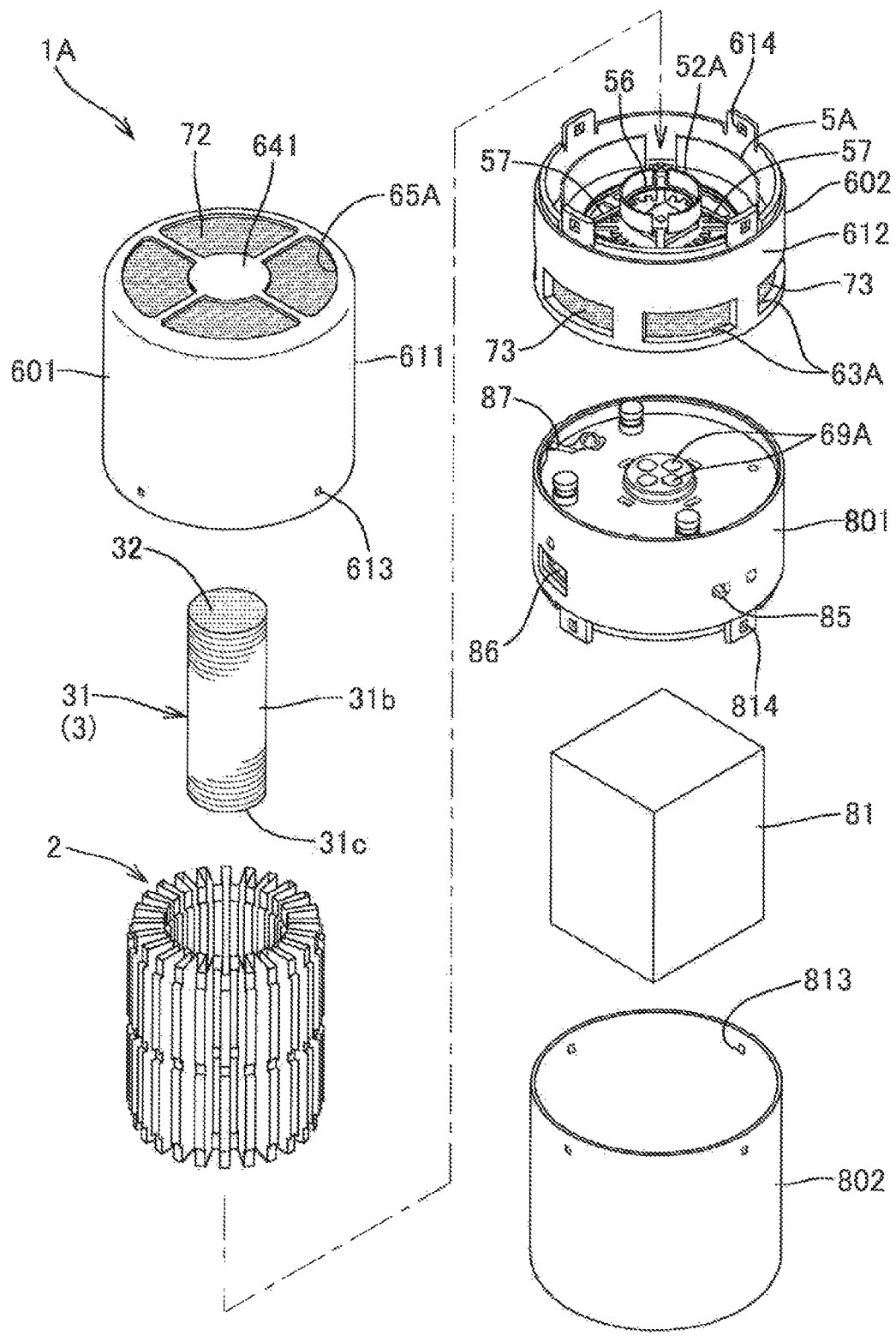
FIG. 12 is an exploded perspective view of the photocatalytic device.

FIG. 10 shows a photocatalytic device 1A according to a modification in which a plurality of (two in this modification) photocatalytic filters 2 are provided along the axial direction in a unit U1. In this modification, a plurality of light emission units 3 are provided so as to correspond to the photocatalytic filters 2. However, only one light irradiation unit 3 may be provided for two or more photocatalytic filters 2 by elongating a light guide member 31 so as to penetrate the two or more photocatalytic filters 2. Alternatively, although not illustrated, a plurality of cylindrical photocatalytic filters having different diameters may be stacked coaxially in the radial direction.

Next, the second embodiment of the present invention will be described with reference to FIG. 11 to FIG. 16.

In a photocatalytic device 1A according to the second embodiment, a housing 6A having a photocatalytic filter 2 and a light irradiation unit 3 disposed therein constitutes a photocatalytic device unit U2 that functions as a photocatalytic device when externally supplied with power. In contrast to the unit U1 of the first embodiment, the unit U2 is configured such that the housing 6A is separable into an upper housing 601 and a lower housing 602. The upper housing 601 includes: an upper peripheral wall 611 having an inner reflection wall 4 that faces the photocatalytic filter 2 and the light guide member 31; and a lid part 641 having ventilation windows 65A at an upper end thereof. The wall 611 and the lid part 641 are integrally formed. The lower housing 602 includes: a lower peripheral wall 612 that has ventilation windows 63A, and surrounds a fan 7, a light source 30, and a support member 5A that supports one ends 2c, 31c (lower ends in the drawings) of the photocatalytic filter 2 and the light guide member 31, and the light source 30; and a bottom plate 62 having hook slots 67 and connection terminals 68A to be electrically connected to connection terminals 69A in a power supply case 8A. The wall 612 and the bottom plate 62 are integrally formed.

The housing 6A being vertically separable as described above facilitates assembly, disassembly, and cleaning, partial reuse, replacement, etc., of the photocatalytic filter 2, the light irradiation unit 3, the fan 7, etc., thereby reducing manufacturing cost and improving convenience. Joint portions of the upper housing 601 and the lower housing 602 are provided with projections 613 and recesses 614 that catch and hold the projections 613.

Figure 13:
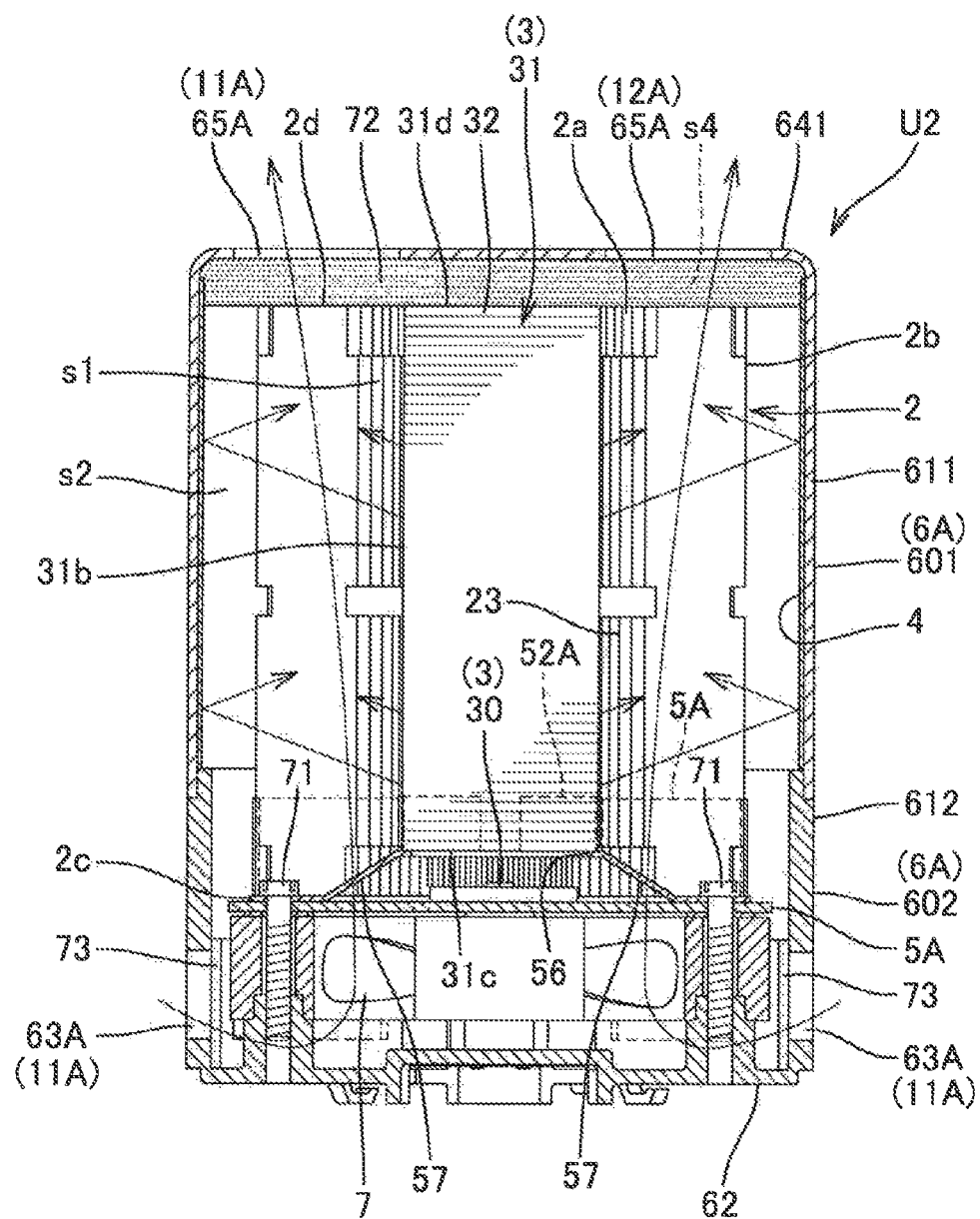
FIG. 13 is a vertical cross-sectional view of a photocatalytic device unit constituting the photocatalytic device.
Figure 14:
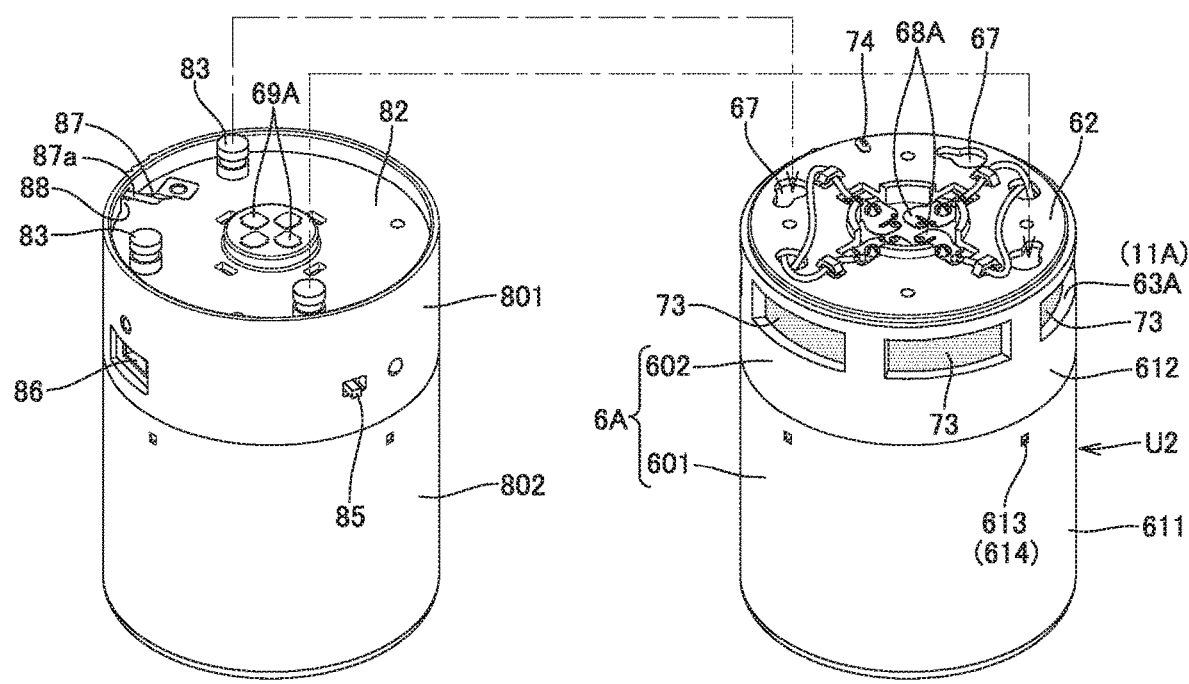
FIG. 14 is a perspective view showing a state where the unit constituting the photocatalytic device is separated from a power supply case.
Figure 15:
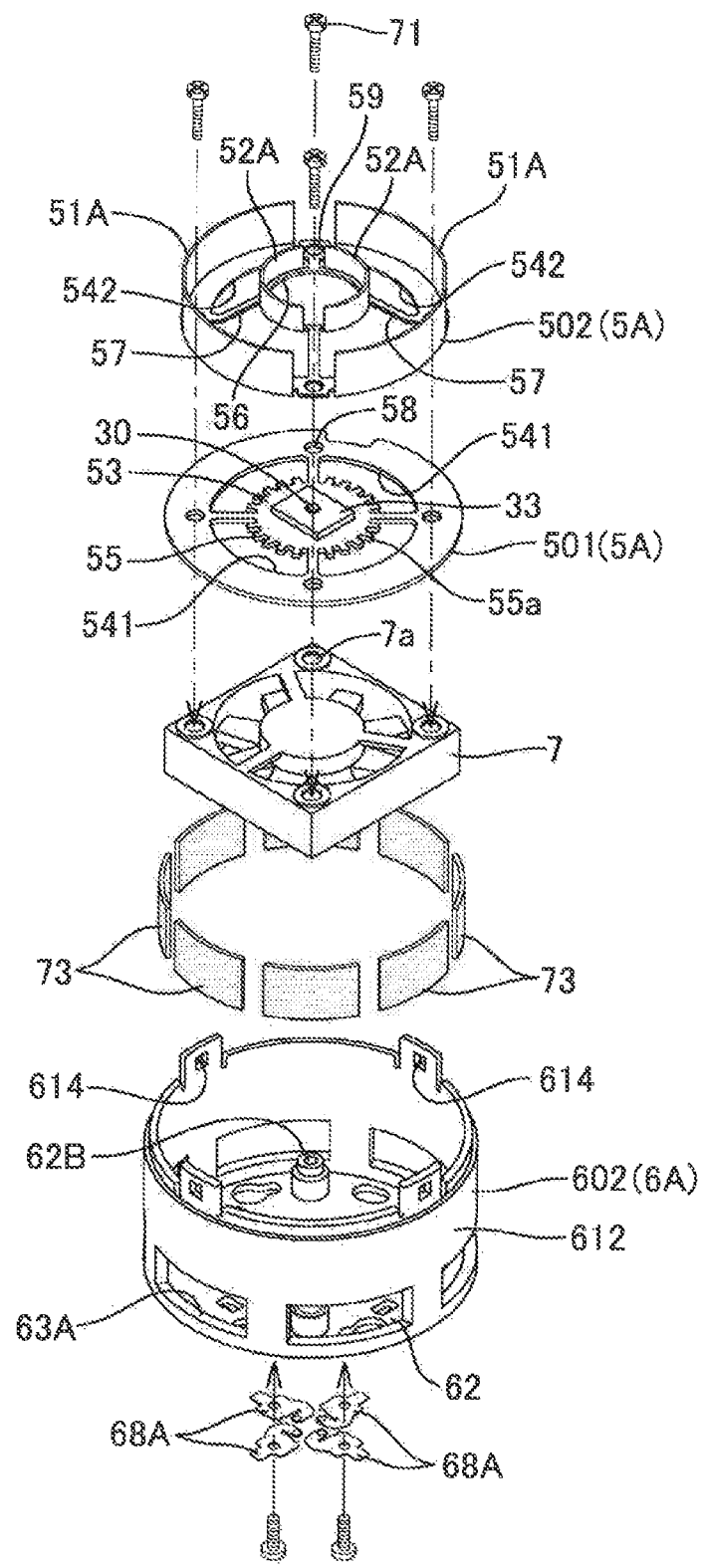
FIG. 15 is an exploded perspective view showing a lower housing and an internal structure thereof.
Figure 16:
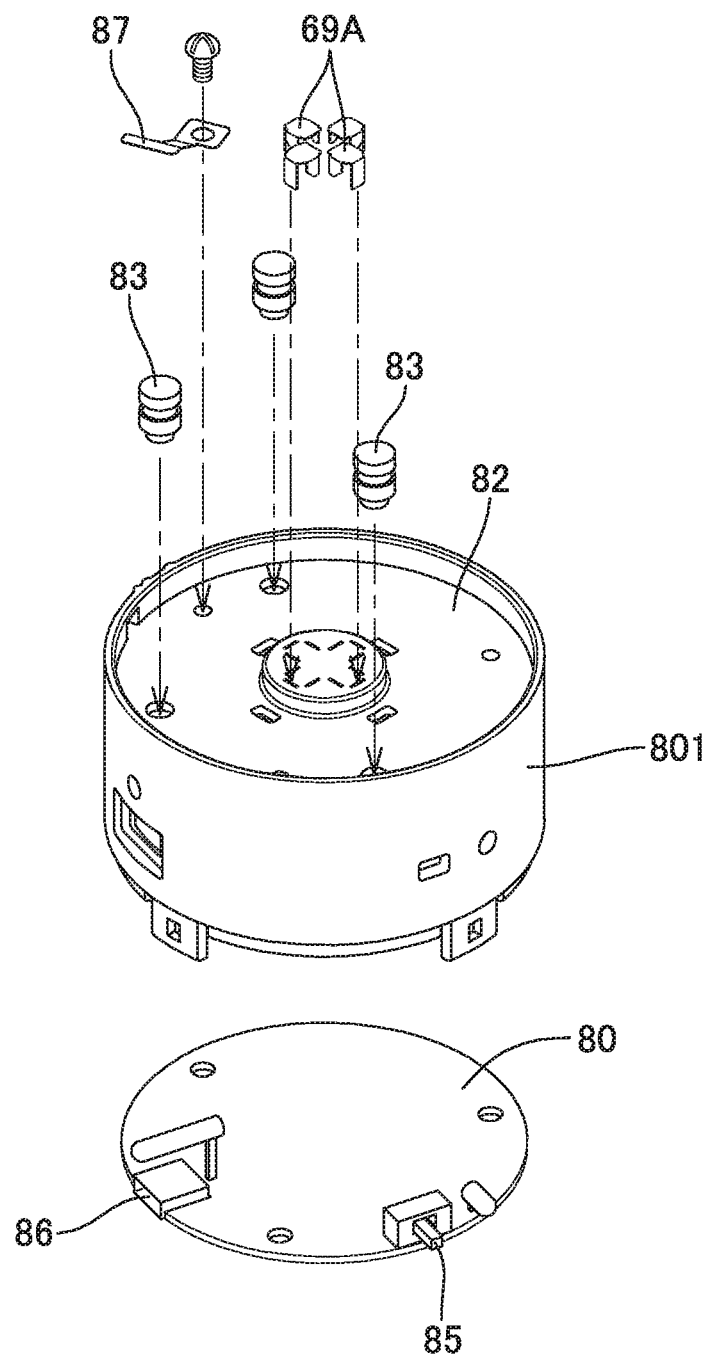
FIG. 16 is an exploded perspective view showing the structure of an upper case.

An activated carbon filter 72 is attached over the entire inner surface of the lid part 641 of the upper housing 601 so as to cover the ventilation windows 65A. This filter 72 purifies the gas discharged from the housing 6A, and prevents the light emitted from the light irradiation unit 3 from leaking to the outside through the ventilation windows. As shown in FIG. 13, this filter 72 is interposed to be held between the lid part 641 of the upper housing 601, and the photocatalytic filter 2 and the light guide member 31, and is replaceable when the upper housing 601 is separated from the lower housing 602. More preferably, the activated carbon filter 72 is obtained by knitting activated carbon fibers.

A dust collecting filter 73 is attached to each of the ventilation windows 63A of the lower housing 602 so as to cover the ventilation window 63A. In this embodiment, the dust collecting filter 73 is pasted to the inner edge of each ventilation window 63A. Alternatively, a sheet of the dust collecting filter 73 may be made annular and pasted over the entire inner surface. Still alternatively, each dust collecting filter 73 may be detachably attached to the ventilation window 63A by using, for example, guide pieces for insertion of the filter 73.

The support member 5A that supports the photocatalytic filter 2 and the light irradiation unit 3 is configured to be separable into a planar metallic first support member 501 and a stereoscopic metallic second support member 502. The first support member 501 has, in the center thereof, a mounting part 55 having a mounting surface 53 on which an LED substrate 33 is mounted, and has a plurality of vent holes 541 formed around the mounting part 55. The second support member 502 is mountable to the upper surface of the first support member 501. The second support member 502 has, at an outer position, first holding pieces 51A, projecting in the axial direction, for holding the outer peripheral surface of a portion at the one end 2c (lower end in the drawings) of the photocatalytic filter 2, and has, at an inner position, second holding pieces 52A, projecting in the axial direction, for holding the outer peripheral surface of a portion at the one end 31c (lower end in the drawings) of the light guide member 31 of the light irradiation unit 3. Vent holes 542 are provided in an area between the first holding pieces 51A and the second holding pieces 52A. A through-hole 56 that allows light emitted from the light source 30 to reach the light guide member 31 is provided in an area surrounded by the second holding pieces 52A.

The support member 5A being separable as described above facilitates setting of an appropriate gap (distance) between the light source 30 and the end portion of the light guide member 31, and also facilitates manufacturing, thereby achieving cost reduction. Projections and recesses 55a are formed at a peripheral edge, facing the vent holes 541, of the mounting part 55 of the first support member 501, so that heat generated from the light source 30 can be efficiently discharged into the gas passing through the vent holes 541. The first support member 501 can be easily manufactured through punching of a raw member, for example.

The second support member 502 has a plurality of holding pieces 51A along the circumferential direction, and a plurality of holding pieces 52A along the circumferential direction. The second support member 502 may have a single annular holding piece 51A and/or a single annular holding piece 52A. The second support member 502 has a plurality of vent holes 542 corresponding to the respective vent holes 541 of the first support member 501. The holding pieces 52A are offset upward in the axial direction with respect to the holding pieces 51A, so that a gap is maintained between the light source 30 mounted to the first support member 501 and the end portion of the light guide member 31. This offset in the axial direction is realized by tilting, in the axial direction, a plurality of connection parts 57 that connect the outer area where the holding pieces 51A are provided with the inner area where the holding pieces 52A are provided. The second support member 502 can be easily and efficiently manufactured through punching and pressing.

The fan 7, the first support member 501, and the second support member 502 have a plurality of sets of through-holes 7a, 58, and 59 formed at corresponding communication positions in the outer areas thereof, and are fixed in the lower housing 602 by mounting screws 71 that penetrate these through-holes and are fitted into screw holes 62b formed at corresponding positions in the bottom plate 62 of the lower housing 602.

The power supply case 8A of this embodiment is configured to be separable into an upper case 801 and a lower case 802, like the housing 6A. The upper case 801 accommodates a control board 80, and has a switch 85, a USB connector 86, etc., exposed at the outer peripheral surface thereof. The lower case 802 accommodates a batten 81. The power supply case 8A being vertically separable as described above facilitates assembly, disassembly and cleaning, partial reuse, replacement, etc., of the control board, the battery, etc., inside the power supply case 8A, thereby reducing manufacturing cost and improving convenience. Joint portions of the upper case 801 and the lower case 802 are provided with projections 813 and recesses 814 that catch and hold the projections 813.

The configuration for assembling the unit U2 to the power supply case 8A and the configuration for electrical connection therebetween are basically identical to those of the first embodiment shown in FIG. 9. In this second embodiment, however, as a lock mechanism in the assembled state, a plate spring 87 that is bent to almost have the shape of "<" is disposed on the upper plate 82 of the power supply case 8A, and a locking projection 74 is disposed on the bottom plate 62 of the unit U2 at a position corresponding to the plate spring 87. When the engagement projections 83 on the power supply case side are inserted in the hook slots 67 on the unit U2 side and are relatively rotated, an end of the plate spring 87 climbs over the locking projection 74, thereby locking the unit U2 with the case 8A in a reversely rotatable manner. An operation piece 87a is provided at an end portion of the plate spring 87 so as to penetrate a through-hole 88 of the upper case 801 and project from the outer peripheral surface in a manner of forming an L-shape. When the projecting operation piece 87a is pushed down with a finger toward the lower case 802, engagement of the plate spring 87 with the locking projection 74 is released, which enables the aforementioned reverse rotation, and thus the unit U2 can be separated from the power supply case 8A. This lock mechanism prevents the unit U2 and the power supply case 8A from being unnecessarily separated from each other.

Since other components, modifications, effects, and the like of the second embodiment are basically identical to those of the first embodiment, the same components are denoted by the same reference characters, and description thereof is omitted.

Figure 17:
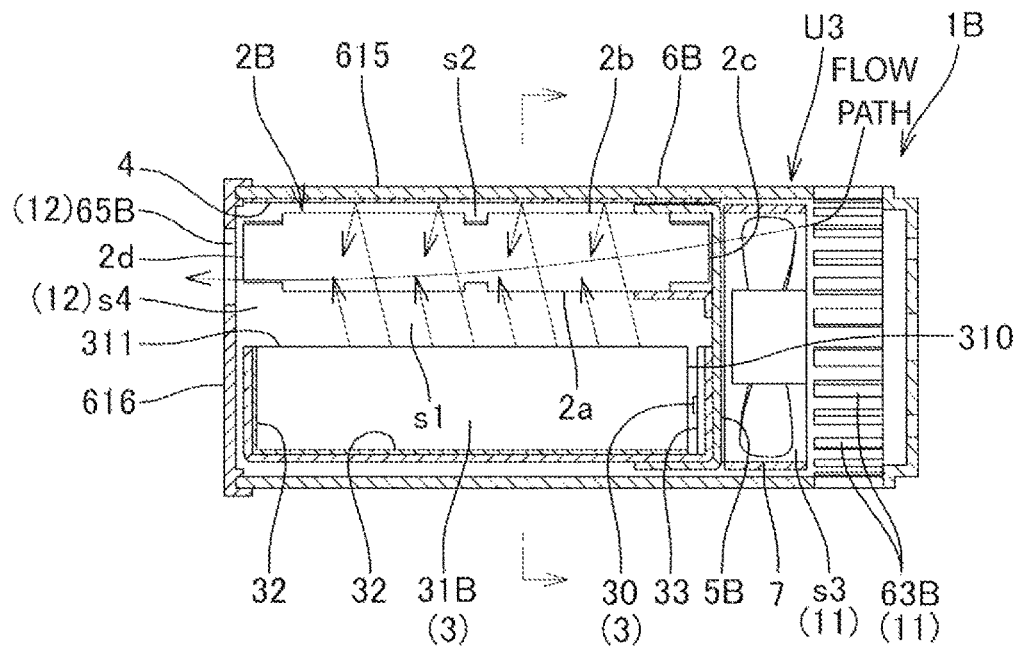
FIG. 17 is a vertical cross-sectional view of a photocatalytic device according to the third embodiment of the present invention, taken along the direction in which ridges or valleys extend.
Figure 18:
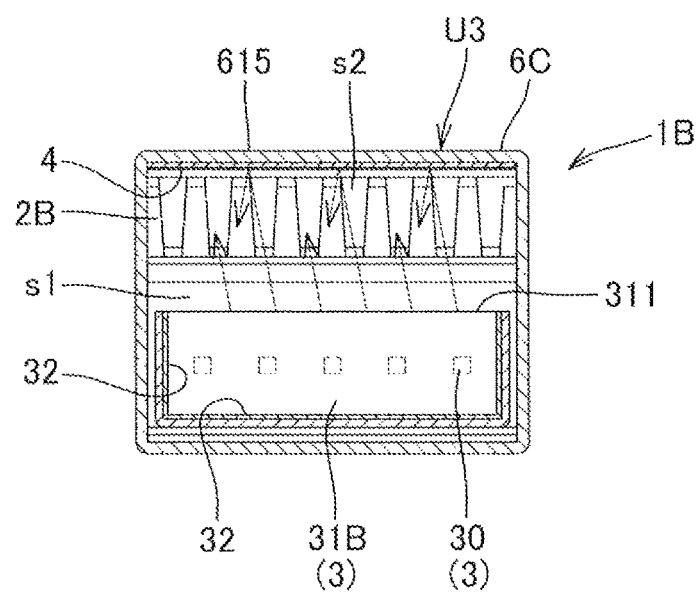
FIG. 18 is a vertical cross-sectional view of the photocatalytic device, taken along the direction orthogonal to the direction in which the ridges or the valleys extend.

The third embodiment of the present invention will be described with reference to FIG. 17 and FIG. 18.

In a photocatalytic device 1B according to the third embodiment, a photocatalytic filter 29 is used in a flat state as shown in FIG. 6, without being rounded in a cylindrical shape as in the first and second embodiments. Also, instead of the cylindrical light guide member 31, a flat light guide member 31B is adopted and arranged in parallel to the photocatalytic filter 2B.

A housing 6C has a box shape. The flat photocatalytic filter 2B is disposed in an internal area on the upper side in FIG. 17, and the flat light guide member 31B is disposed in parallel to and away from the photocatalytic filter 2B in the internal area on the lower side. Instead of using the light guide member 31B, a plate-shaped LED substrate on which LED elements as light sources are disposed at predetermined intervals may also be preferably used.

The light guide member 319 has an end surface 310 on the same side as one end 2c of the photocatalytic filter 2B in the direction in which ridges and valleys extend, and this end surface 310 serves as an incident surface on which light from the opposed light source 30 enters. The light guide member 31B is provided with a light shielding layer 32 whose inner surface serves as a reflection surface, on the surface excluding the end surface 310 and a light radiation surface 311 facing the photocatalytic filter 2B.

Light emitted from a light emitting surface (light radiation surface 311) of the light guide member 31B and applied to the filter surface 2a activates the photocatalyst on the surface 2a, passes through the light-passing holes of the filter 2B to reach the other surface side, is reflected by the reflection wall 4 that is the inner surface of an upper wall 615 of the housing 6C, is applied to the entirety of the other surface 2b of the photocatalytic filter 2B, and activates the photocatalyst on the surface 2b. As for the reflection wall 4, the surface of the metal material of the housing may be used as is, or after being subjected to mirror finishing, or a mirror sheet may be adhered to the inner surface of the upper wall 615.

Since the end portions of the photocatalytic filter 2 and the light irradiation unit 3, on the one end 2c side, are supported by a metallic support member 5B in the housing 6C, heat generated in the light irradiation unit 3 is transferred to the metallic photocatalytic filter 2B through the support member 5B, and is efficiently discharged from the surface of the photocatalytic filter 2B into the gas. That is, according to the present embodiment, the support member 5B and the photocatalytic filter 2B can efficiently function as heatsinks.

The support member 5B is provided with a vent hole (not shown) communicating with upper and lower spaces s2, s1 of the photocatalytic filter 2B. In an area, inside the housing, on the side opposite to the photocatalytic filter 2B with respect to the support member 5B, a fan 7 that forcibly feeds the gas into the vent hole is provided. In addition, on upper, lower, left, and right walls of the housing on the side opposite to the support member 5B with respect to the fan 7, a plurality of ventilation windows 63B penetrating the housing are provided, whereby the gas can be taken into the housing from the outside. The fan 7 draws the external gas into the housing through the ventilation windows 639, and feeds the gas into the spaces s1, s2 through the vent hole.

A ventilation window 65B that allows the spaces s1, s2 to communicate with the outside of the housing is formed penetrating a wall 616 of an end portion, of the housing 6B, facing the other end 2d of the photocatalytic filter 2B. Thus, the gas, which has entered the housing through the ventilation windows 63B and flowed into the spaces s1, s2, flows in the spaces s1, s2 toward the other end 2d along the direction in which the ridges 21 and the valleys 22 of the photocatalytic filter 2B extend, and thereafter is discharged from the housing through the ventilation window 65B.

While flowing in the spaces s1, s2, the gas efficiently contacts the corrugated front and rear surfaces 2a, 2b of the photocatalytic filter 2B, and is efficiently purified by the photocatalyst on the front and rear surfaces 2a, 2b, which is activated while being irradiated with light. The ventilation windows 63B that allow the gas to flow into the housing, and a space s3 between the ventilation windows 63B and the one end 2c of the photocatalytic filter function as gas inflow parts 11, While the ventilation window 65B and a space s4 between the other end 2d of the photocatalytic filter and the end wall 616 function as gas outflow parts 12.

Thus, in the housing 6B, light is applied to the photocatalytic filter 2B from the lower side toward the upper side, so that the inner and outer surfaces of the filter 2B are irradiated with the light through the light-passing holes, Meanwhile, the gas flows through the spaces s1, s2 serving as flow channels at both the front and rear surfaces along the axial direction (direction in which the ridges 21 and the valleys 22 extend) intersecting the light emission direction, and the gas is efficiently purified by the activated photocatalyst while the gas flows. In the present invention, this intersecting configuration allows the spaces s1, s2 to be set small, whereby the whole device can be miniaturized.

In this embodiment, the housing 6B having the photocatalytic filter 2B and the light irradiation unit 3 disposed therein constitutes a single photocatalytic device unit U3 that functions as a photocatalytic device when being supplied with power from the outside. When a power supply case having a box shape similar to the photocatalytic device unit U3 is connected to the unit U3 as in the first and second embodiments, the unit U3 can be driven with power from a battery inside the power supply case.

Since other components, modifications, effects, and the like of the third embodiment are basically identical to those of the first and second embodiments, the same components are denoted by the same reference characters, and description thereof is omitted.

Next, the fourth embodiment of the present invention will be described with reference to FIG. 19.

Figure 19:
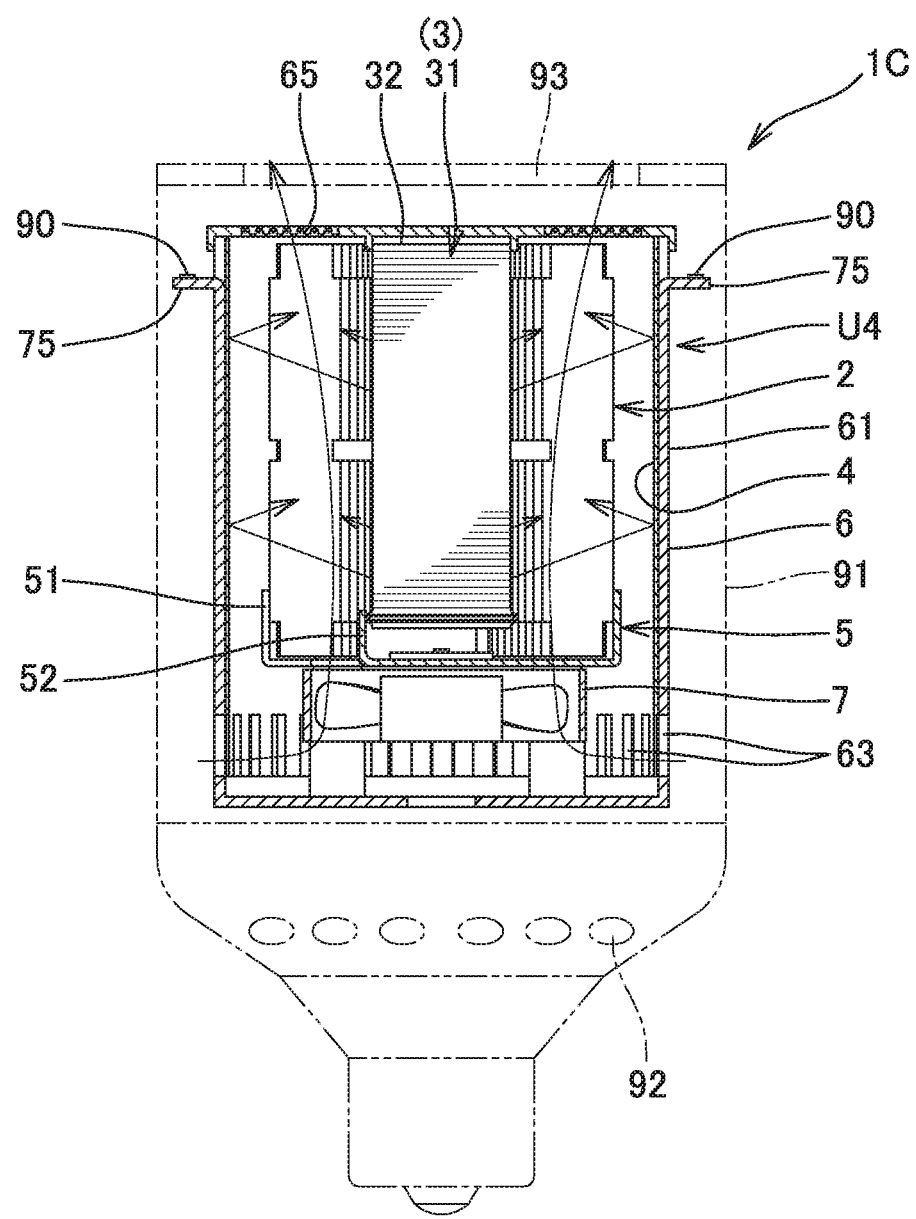
FIG. 19 is a vertical cross-sectional view showing a photocatalytic device according to the fourth embodiment of the present invention.

As shown in FIG. 19, a photocatalytic device 1C according to the present embodiment is configured as a photocatalytic device that functions as a lighting device (lamp) by using a unit U4 having almost the same structure as the unit U1 of the first embodiment.

As for power to be supplied, power of the lighting device (lamp) can be used. In this embodiment, for example, a portion of the peripheral wall 61 of the housing 6 of the unit U4 is cut and raised to form a placement piece 75 that projects from the outer peripheral surface of the housing 6, so as to allow a light source 90 for lighting to be placed. A transparent lens body is provided around the unit U4. Inlet ports 92 for introducing external air and exhaust ports 93 for discharging the air are provided through the lens housing 91 at positions corresponding to the ventilation windows 63 and 65 of the unit U4, respectively. These inlet ports 92 and the exhaust ports 93 are preferably provided with a dust protection filter and/or a light protection net.

The light source 90 for lighting need not be disposed on the peripheral wall 61 of the housing as in the present embodiment, and may be disposed on a center portion, of the wall at the upper end of the housing, which is surrounded by the ventilation windows 65, or on other parts. It is also preferable to provide a human sensor, and control the photocatalytic device such that, when the sensor does not detect any human, only lighting is turned off while continuing the operation as the photocatalytic device. The photocatalytic device configured as a lighting device according to the present embodiment s suitable to be used in a small space such as a toilet.

Since other components, modifications, effects, and the like of the fourth embodiment are basically identical to those of the first and second embodiments, the same components are denoted by the same reference characters, and description thereof is omitted.

The embodiments of the present invention have been described above. However, the present invention is by no means limited to the embodiments, and can be incorporated in various kinds of equipment as well as lighting equipment by using a common unit. Thus, the present invention can be implemented, as a matter of course, in various forms without departing from the gist of the present invention.

DESCRIPTION OF THE REFERENCE CHARACTERS 1, 1A, 1B, 1C photocatalytic device
2, 2B photocatalytic filter
2a, 2b filter surface
2c one end
2d the other end
3 light irradiation unit
4 reflection wall
5, 5A, 5B support member
6, 6A, 6B, 6C housing
7 fan
7a through-hole
8, 8A power supply case
11 inflow part
12 outflow part
20 member
21 ridge
22 valley
23 light-passing hole
24 upright piece
25 bridge
30 light source
31, 31B light guide member
31b outer peripheral surface
31c one end
31d the other end
32 light shielding layer
33 substrate
51, 51A holding piece
52, 52A holding piece
53 mounting surface
54 vent hole
55 mounting part
55a projections and recesses
56 through-hole
57 connection part
61 peripheral wall
62 bottom plate
62b screw hole
63, 63A, 63B ventilation window
64 lid member
65, 65A, 65B ventilation window
66 through-hole
67 hook slot
68, 68A connection terminal
69, 69A connection terminal
70 leg member
71 mounting screw
72 activated carbon filter
73 dust collecting filter
74 locking projection
75 placement piece
80 control board
81 battery
82 upper plate
83 engagement projection
84 through-hole
85 switch
86 connector
87 plate spring
87a operation piece
88 through-hole
90 light source
91 lens housing
92 inlet port
93 exhaust port
310 end surface
311 light radiation surface
501 first support member
502 second support member 541 vent hole
542 vent hole
601 upper housing
602 lower housing
611 upper peripheral wall
612 lower peripheral wall
613 projection
614 locking recess
615 wall
616 wall
641 lid part
801 upper case
802 lower case
813 projection
814 locking recess
s1, s2 space
s3, s4 space
U1, U2, U3, U4 unit

The invention claimed is:

1. A photocatalytic device, comprising:
a photocatalytic filter having a surface on which a photocatalyst is carried, the photocatalytic filter being formed of a corrugated member having a plurality of ridges and a plurality of valleys alternately arranged, the photocatalytic filter having light-passing holes that allow ultraviolet light or visible light to pass therethrough, at top portions of the ridges and bottom portions of the valleys, the light-passing holes being through-grooves elongated in the direction in which the ridges and the valleys extend;
a light irradiation unit configured to irradiate one of front and rear surfaces of the photocatalytic filter with ultraviolet light or visible light;
a reflection wall facing the other one of the front and rear surfaces of the photocatalytic filter, the reflection wall reflecting light that has been emitted from the light irradiation unit and has passed through the light-passing holes that are formed by the ridges and the valleys of the photocatalytic filter, toward the other surface, the reflection wall extending from one end to the other end of the photocatalytic filter; and
a gas inflow part and a gas outflow part respectively provided at one end and the other end of the photocatalytic filter, the gas inflow part and the gas outflow part allowing a gas to flow through in a space between the light irradiation unit and the photocatalytic filter and through another space between the reflection wall and the photocatalytic filter, over the front and rear surfaces of the photocatalytic filter from the one end toward the other end along a direction in which the ridges and the valleys extend, wherein
the light-passing holes of the photocatalytic filter are through-grooves elongated in the direction in which the ridges and the valleys extend, and
upright pieces are formed at paired opening edges which extend along a longitudinal direction of each through-groove and are opposed each other, the upright pieces being cut and raised for forming the through-groove and being erected at a projecting surface of the ridge or the valley.

2. A photocatalytic device, comprising:
a photocatalytic filter having a surface on which a photocatalyst is carried, the photocatalytic filter being formed of a corrugated member having a plurality of ridges and a plurality of valleys alternately arranged, the photocatalytic filter having light-passing holes that allow ultraviolet light or visible light to pass therethrough, at top projecting surfaces of the ridges and bottom projecting surfaces of the valleys, the light-passing holes being through-grooves formed by at least the top projecting surfaces of the ridges or the bottom projecting surfaces of the valleys and elongated in the direction in which the top projecting surfaces of the ridges and the bottom projecting surfaces of the valleys extend;
a light irradiation unit configured to irradiate one of front and rear surfaces of the photocatalytic filter with ultraviolet light or visible light;
a reflection wall facing the other one of the front and rear surfaces of the photocatalytic filter, the reflection wall reflecting light that has been emitted from the light irradiation unit and has passed through the light-passing holes that are formed by the ridges and the valleys of the photocatalytic filter, toward the other surface, the reflection wall extending from one end to the other end of the photocatalytic filter; and
a gas inflow part and a gas outflow part respectively provided at one end and the other end of the photocatalytic filter, the gas inflow part and the gas outflow part allowing a gas to flow through in a space between the light irradiation unit and the photocatalytic filter and through another space between the reflection wall and the photocatalytic filter, over the front and rear surfaces of the photocatalytic filter from the one end toward the other end along a direction in which the ridges and the valleys extend, wherein
the light-passing holes of the photocatalytic filter are through-grooves elongated in the direction in which the ridges and the valleys extend, and
upright pieces are formed at paired opening edges which extend along a longitudinal direction of each through-groove and are opposed each other, the upright pieces being cut and erected from the projecting surfaces of the ridges or the valleys for forming each of the light-passing holes having the through-groove that respectively extends along a projecting surface among the projecting surfaces of the ridges or the valleys.

* * * * *